United States Patent
Dillon et al.

(10) Patent No.: US 6,756,395 B2
(45) Date of Patent: Jun. 29, 2004

(54) IMIDAZOLINYIMETHYL ARALKLSULFONAMIDES

(75) Inventors: Michael Patrick Dillon, San Carlos, CA (US); Clara Jeou Jen Lin, Palo Alto, CA (US); Counde O'Yang, Sunnyvale, CA (US); Xiaoming Zhang, Campbell, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 10/421,119

(22) Filed: Apr. 22, 2003

(65) Prior Publication Data

US 2003/0229130 A1 Dec. 11, 2003

Related U.S. Application Data

(60) Provisional application No. 60/374,700, filed on Apr. 23, 2002, and provisional application No. 60/378,775, filed on May 8, 2002.

(51) Int. Cl.$^7$ .................. A61K 31/4178; C07D 405/06
(52) U.S. Cl. .................. 514/402; 514/401; 548/355.1; 548/349.1; 548/311.4
(58) Field of Search .................. 548/355.1, 349.1, 548/311.4, 350.1; 514/401, 402

(56) References Cited

U.S. PATENT DOCUMENTS

| | | | |
|---|---|---|---|
| 3,660,423 A | * | 5/1972 | Wysong et al. .......... 548/355.1 |
| 6,602,897 B2 | | 8/2003 | Esser et al. |
| 2002/0169193 A1 | | 11/2002 | Pouzet et al. |

FOREIGN PATENT DOCUMENTS

| | | |
|---|---|---|
| EP | 0 887 436 A2 | 12/1998 |
| GB | 1336 228 | 11/1973 |

OTHER PUBLICATIONS

Nardi, D., et al., Hypertensive Activity of 2–(2,3,4,6–tetramethylbenzyl) imidazoline and related compounds, (Research on Durene Derivatives), *Farmaco., Ed. Sci.* (1979) pp. 789–801, vol. 34(9).

Lis, R., et al., "Synthesis and Antiarrhythmic Activity of Novel 3–Alkyl–1–[ω–[4–[(alkylsulfonyl)amino]phenyl]–ω–hydroxyalkyl]–1H–imidazolium Salts and Related Compounds," *J. Med. Chem.*, (1987), pp. 2303–2309, vol. 30.

\* cited by examiner

*Primary Examiner*—Laura L. Stockton
(74) *Attorney, Agent, or Firm*—Robert C. Hall

(57) ABSTRACT

Compounds of the Formula:

where $R^1$–$R^6$ are those defined herein and methods for producing the same. Also provided are pharmaceutical compositions comprising a Compound of Formula I and methods for their use as therapeutic agents.

46 Claims, No Drawings

IMIDAZOLINYIMETHYL ARALKLSULFONAMIDES

CROSS REFERENCE TO RELATED INVENTIONS

This application claims the priority benefit under Title 35 U.S.C. 119(e) of U.S. Provisional Applications Ser. No. 60/374,700, filed Apr. 23, 2002 and Ser. No. 60/378,775, filed May 8, 2002, the disclosures of which are herein incorporated by reference in their entirety.

FIELD OF THE INVENTION

This invention relates to imidazolin-2-ylmethyl substituted arylalkylsulfonamide derivatives, compositions comprising the same, methods for use, and methods of preparation thereof.

BACKGROUND OF THE INVENTION

Alpha-1 ($\alpha_1$) adrenergic receptors (i.e., ($\alpha_1$ adrenoceptors) are G-protein coupled transmembrane receptors that mediate various actions of the sympathetic nervous system through the binding of the catecholamines, epinephrine and norepinephrine (NE). Currently, several subtypes of the $\alpha_1$ adrenergic receptors are known to exist for which the genes have been cloned: $\alpha_{1A}$ (previously known as $\alpha_{1C}$), $\alpha_{1B}$ and ($\alpha_{1D}$. Recently the existence of a low affinity $\alpha_1$ adrenoceptor for prazosin named $\alpha_{1L}$, in human prostate has been determined. However, the gene for the $\alpha_{1L}$ adrenergic receptor subtype has yet to be cloned. The $\alpha_1$ adrenoceptor plays a part in the sympathetic maintenance of smooth muscle tone and $\alpha_1$ adrenergic agonists are known to increase muscle tone in the lower urinary tract (Testa, R., *Eur. J. Phannacol.*, 249, 307–315 (1993). Pharmacological studies resulting in the subdivision of $\alpha_1$ adrenergic receptors have let to the suggestion that development of subtype-selective compounds may allow improved treatment with a lower incidence of side effects.

Urinary incontinence is a condition defined as the involuntary loss of urine. Stress urinary incontinence (SUI) occurs when the internal sphincter does not close completely. The primary symptom is minor leakage from activities, such as coughing, sneezing, laughing, running, lifting, or even standing, that apply pressure to a full bladder. Leakage stops when the activity stops. SUI is most common in women between the ages of 25 and 50, and many regularly exercising women have some degree of SUI.

The present methods to treat SUI include physiotherapy and surgery. Treatment with pharmaceuticals is limited to the use of non-selective adrenergic agonists.

Only a limited number of pharmaceutical agents have been employed, with varying success, to treat stress incontinence.

Phenylpropanolamine, pseudoephedrine and midodrine are considered first-line therapy for mild to moderate stress incontinence (Wein, supra; Lundberg (editor), *JAMA*, 1989, 261(18), 2685–2690). These agents are believed to work both by direct activation of $\alpha_1$ adrenoceptors and indirectly by displacement of endogenous norepinephrine from sympathetic neurons following uptake into the nerve terminal (Andersson and Sjogren, *Progress in Neurobiology*, 1982, 71–89). Activation of $\alpha_1$ adrenoceptors located on the smooth muscle cells of the proximal urethra and bladder neck (Sourander, *Gerontology*, 1990, 36, 19–26; Wein, supra) evokes contraction and an increase in urethral closure pressure.

The utility of phenylpropanolamine, pseudoephedrine, and midodrine is limited by a lack of selectivity among the $\alpha_1$ adrenoceptor subtypes and by the indirect action of these agents (i.e., activation of $\alpha_1$, $\alpha_2$, and $\beta$-adrenoceptors in the central nervous system and periphery). As a result, any desired therapeutic effect of these agents may be accompanied by undesirable side effects, such as an increase in blood pressure. The increase in blood pressure is dose-dependent and therefore limits the ability to achieve therapeutically effective circulating concentrations of these agents (Andersson and Sjogren, supra). Furthermore, in some patients these agents produce insomnia, anxiety and dizziness as a result of their central nervous system stimulant actions (Andersson and Sjogren, supra, Wein, supra).

While some selective $\alpha_{1A}$ agonists have recently been disclosed for the treatment of stress incontinence, there continues to be a need for medicaments that are useful for the treatment of incontinence. A compound having the desired $\alpha_{1A}$ adrenergic agonist profile is desirable.

SUMMARY OF THE INVENTION

One aspect of the present invention provides a compound of the formula:

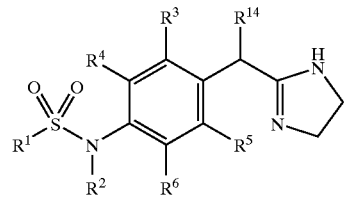

I a pharmaceutically acceptable salt or a prodrug thereof, wherein
$R^1$ is alkyl, —$NR^7R^8$, where each of $R^7$ and $R^8$ is independently hydrogen or alkyl;
$R^2$ is hydrogen or alkyl;
each of $R^3$, $R^4$, $R^5$, and $R^6$ is independently hydrogen, halide, alkyl, —$OR^9$ (where $R^9$ is hydrogen, alkyl, a hydroxy protecting group, or cycloalkylalkyl), —$SR^{10}$ (where $R^{10}$ is hydrogen or alkyl), or —$NR^{11}R^{12}$ (where each of $R^{11}$ and $R^{12}$ is independently hydrogen, alkyl, or a nitrogen protecting group), provided $R^3$, $R^4$, $R^5$, and $R^6$ are not all simultaneously alkyl); or $R^3$ and $R^4$ together with atoms to which they are attached to form heterocyclyl, heteroaryl, or cycloalkyl; and
$R^{14}$ is hydrogen, lower alky, or —$OR^{15}$ (where $R^{15}$ is hydrogen, lower alkyl, or a hydroxy protecting group).

Preferably $R^{14}$ is hydrogen, methyl or hydroxy. More preferably $R^{14}$ is hydrogen.

In one embodiment of the present invention, $R^1$ is alkyl. Preferably, $R^1$ is selected from the group consisting of methyl, ethyl, and isopropyl.

In another embodiment, $R^2$ is hydrogen.

Yet in another embodiment, each of $R^7$ and $R^8$ is independently hydrogen or methyl.

Still in another embodiment, each of $R^3$, $R^4$, $R^5$, and $R^6$ is independently hydrogen, halide, alkyl, or —$OR^{10}$, where $R^{10}$ is hydrogen, alkyl, a hydroxy protecting group, or cycloalkylalkyl; or $R^3$ and $R^4$ together with atoms to which they are attached to form heterocyclyl, heteroaryl, or cycloalkyl. Preferably, at least one of $R^3$, $R^4$, $R^5$, and $R^6$ is alkyl, halide, or —$OR^9$, where $R^9$ is as defined above. More preferably, at least one of $R^3$, $R^4$, $R^5$, and $R^6$ is bromo, chloro, fluoro, methoxy, ethoxy, methyl, or hydroxy.

In one specific embodiment of the present invention, (a) $R^3$ is methoxy, and $R^4$, $R^5$, and $R^6$ are hydrogen;

(b) $R^3$ is methyl, $R^6$ is methoxy, and $R^4$ and $R^5$ are hydrogen;

(c) $R^3$ is methyl, $R^6$ is chloro, and $R^4$ and $R^5$ are hydrogen;

(d) $R^3$ is chloro, $R^4$ is methoxy, and $R^5$ and $R^6$ are hydrogen;

(e) $R^3$ is methyl, $R^4$ is chloro, and $R^5$ and $R^6$ are hydrogen;

(f) $R^3$ is methyl, $R^4$ is methoxy, and $R^5$ and $R^6$ are hydrogen;

(g) $R^4$ is chloro, and $R^3$, $R^5$ and $R^6$ are hydrogen;

(h) $R^4$ is methoxy, and $R^3$, $R^5$, and $R^6$ are hydrogen;

(i) $R^3$ is methyl, $R^6$ is bromo, and $R^4$ and $R^5$ are hydrogen;

(j) $R^3$ is bromo, $R^4$ is methoxy, and $R^5$ and $R^6$ are hydrogen;

(k) $R^3$ is methyl, $R^4$ is bromo, and $R^5$ and $R^6$ are hydrogen; or (l) $R^4$ is bromo, and $R^3$, $R^5$ and $R^6$ are hydrogen.

In another embodiment, $R^3$ and $R^4$ together with atoms to which they are attached to form furanyl, dihydrofuranyl, pyrrolyl, or phenyl. Preferably, $R^3$ and $R^4$ together with atoms to which they are attached to form furanyl or dihydrofuranyl. Preferred examples include:

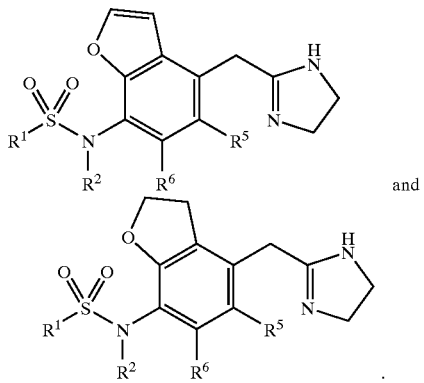

and

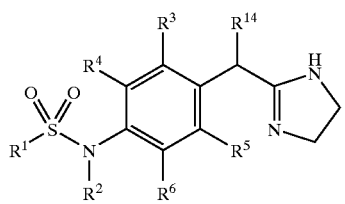

Preferably, Compound of Formula I has an $IC_{50}$ $\alpha_{1A/L}$ receptor agonist activity of about 1 μM or less.

Another aspect of the present invention provides a method for producing an imidazolin-2-ylmethyl-substituted aromatic compound of the formula:

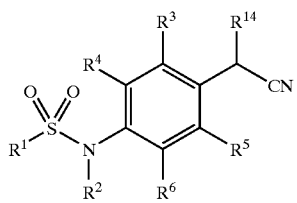

said method comprising contacting a nitrile compound of the formula:

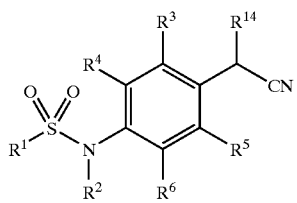

with ethylene diamine to produce the imidazolin-2-ylmethyl-substituted aromatic compound,
wherein
$R^1$ is alkyl, $-NR^7R^8$, where each of $R^7$ and $R^8$ is independently hydrogen or alkyl;
$R^2$ is hydrogen or alkyl;
each of $R^3$, $R^4$, $R^5$, and $R^6$ is independently hydrogen, halide, alkyl, $-OR^9$, where $R^9$ is hydrogen, alkyl, a hydroxy protecting group, or cycloalkylalkyl, $-SR^{10}$, where $R^{10}$ is hydrogen or alkyl, or $-NR^{11}R^{12}$, where each of $R^{11}$ and $R^{12}$ is independently hydrogen, alkyl, or a nitrogen protecting group; or $R^3$ and $R^4$ together with atoms to which they are attached to form heterocyclyl, heteroaryl, or cycloalkyl; and
$R^{14}$ is hydrogen, lower alkyl, or $-OR^{15}$, where $R^{15}$ is hydrogen, lower alkyl, or a hydroxy protecting group.

Yet another aspect of the present invention provides a method for producing an imidazolin-2-ylmethyl-substituted aromatic compound of the formula:

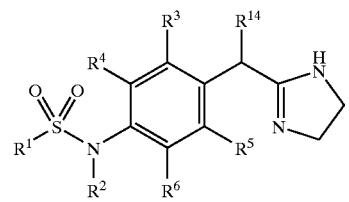

said method comprising contacting an ester compound of the formula:

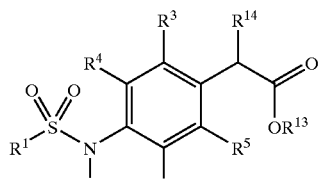

with ethylene diamine in the presence of a trialkylaluminum to produce the imidazolin-2-ylmethyl-substituted aromatic compound,
wherein
$R^1$ is alkyl, $-NR^7R^8$, where each of $R^7$ and $R^8$ is independently hydrogen or alkyl;
$R^2$ is hydrogen or alkyl;
each of $R^3$, $R^4$, $R^5$, and $R^6$ is independently hydrogen, halide, alkyl, $-OR^9$, where $R^9$ is hydrogen, alkyl, a hydroxy protecting group, or cycloalkylalkyl, $-SR^{10}$, where $R^{10}$ is hydrogen or alkyl, or $-NR^{11}R^{12}$, where each of $R^{11}$ and $R^{12}$ is independently hydrogen, alkyl, or a nitrogen protecting group; or $R^3$ and $R^4$ together with atoms to which they are attached to form heterocyclyl, heteroaryl, or cycloalkyl;

$R^{13}$ is alkyl; and $R^{14}$ is hydrogen, lower alkyl, or —$OR^{15}$, where $R^{15}$ is hydrogen, lower alkyl, or a hydroxy protecting group.

Preferably, the trialkylaluminum is trimethylaluminum or triethylaluminum.

Another aspect of the present invention provides a composition comprising:

(a) a therapeutically effective amount of a Compound of Formula I; and (b) a pharmaceutically acceptable carrier.

Preferably, the Compound of Formula I in the pharmaceutical composition is $\alpha_{1A/L}$ receptor agonist.

Still another aspect of the present invention provides a method for treating a patient having a disease state that is alleviated by treatment with an $\alpha_{1A/L}$ receptor agonist, wherein said method comprises administering to the patient a therapeutically effective amount of a Compound of Formula I.

In one particular embodiment, wherein the disease state is selected from the groups consisting of urge incontinence, stress incontinence, overflow incontinence, functional incontinence, sexual dysfunction, nasal congestion, and CNS disorders selected from the group depression, anxiety, dementia, senility, Alzheimer's, deficiencies in attentiveness and cognition, eating disorders, obesity, bulimia and anorexia.

Yet another aspect of the present invention provides a method for treating a disease state comprising urinary incontinence by administering to a subject in need of such treatment an effective amount of a Compound of Formula I.

In one particular embodiment, the disorder is stress incontinence.

In another embodiment, the disorder is urge incontinence.

Still yet another aspect of the present invention provides a method for treating nasal congestion by administering to a mammal in need of such treatment an effective amount of a Compound of Formula I.

In one embodiment, the disorder is nasal congestion.

In another embodiment, the disorder is sinusitis or otitis.

Further aspect of the present invention provides a method for treating sexual dysfunction by administering to a mammal in need of such treatment an effective amount of a Compound of Formula I.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a monovalent linear or branched saturated hydrocarbon moiety, consisting solely of carbon and hydrogen atoms, having from one to twelve carbon atoms inclusive, unless otherwise indicated. Examples of alkyl moieties include, but are not limited to, methyl, ethyl, propyl, isopropyl, isobutyl, sec-butyl, tert-butyl, pentyl, n-hexyl, octyl, dodecyl, and the like. "Lower alkyl" means an alkyl radical having one to five carbon atoms.

"Alkylene" means a divalent linear or branched saturated hydrocarbon moiety, consisting solely of carbon and hydrogen atoms, having from one to six carbons inclusive, unless otherwise indicated. Examples of alkylene moieties include, but are not limited to, methylene, ethylene, propylene, 2-methyl-propylene, butylene, 2-ethylbutylene, and the like.

"Aryl" means a monovalent cyclic aromatic hydrocarbon moiety consisting of one or more fused rings in which at least one ring is aromatic in nature, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl moieties include, but are not limited to, phenyl, naphthyl, biphenyl, indanyl, anthraquinolyl, and the like.

"Cycloalkyl" means a non-aromatic, preferably saturated, carbocyclic moiety consisting of one or more rings, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of cycloalkyl moieties include, but are not limited to, cyclopropyl, cyclobutyl, 3-ethylcyclobutyl, cyclopentyl, cyclopentyl, cycloheptyl, and the like.

"Heteroaryl" means an aromatic carbocyclic moiety having one or more rings incorporating one, two, or three heteroatoms (chosen from nitrogen, oxygen, or sulfur) within the aromatic ring. The heteroaryl can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heteroaryl moieties include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, quinolinyl, isoquinolinyl, quinuclidinyl, naphtyridinyl, and the like.

"Heterocyclyl" means a non-aromatic, carbocyclic moiety, consisting of one or more rings, incorporating one, two, or three heteroatoms (chosen from nitrogen, oxygen or sulfur) within the ring moiety. Heterocyclyl can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heterocyclic moieties include, but are not limited to, dihydrofuranyl, morpholinyl, piperazinyl, piperidinyl, pyrrolidinyl, tetrahydropyranyl, thiomorpholinyl, and the like.

The terms "halogen" and "halide" are used interchangeably herein and refer to fluoro, bromo, chloro, or iodo.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means a group which selectively blocks one reactive site in a multifunctional compound such that a chemical reaction can be carried out selectively at another unprotective reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters.

"Nitrogen protecting group" means a protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate; or by catalytic hydrogenation in the case of CBZ. Suitable nitrogen protecting groups are well known to one skilled in the art. See, for example, *Protective Groups in Organic Synthesis*, 3rd edition, T. W. Greene and P. G. M. Wuts, John Wiley & Sons, New York, 1999, which is incorporated herein by reference in its entirety.

"Hydroxy-protecting group" means a protecting group, other than alkyl, that preserves a hydroxy group that otherwise would be modified by certain chemical reactions. Suitable hydroxy-protecting groups include ether-forming groups that can be removed easily after completion of all other reaction steps, such as the benzyl or the trityl group optionally substituted in their phenyl ring. Other suitable hydroxy-protecting groups include tetrahydropyranyl, silyl, trialkylsilyl ether groups, and the allyl group. Suitable hydroxy protecting groups are well known to one skilled in the art. See, for example, the above incorporated *Protective Groups in Organic Synthesis*, 3rd edition, T. W. Greene and P. G. M. Wuts, John Wiley & Sons, New York, 1999.

"Deprotection" or "deprotecting" means a process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Inert organic solvent" or "inert solvent" means a solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive or less active form of a compound which must be metabolized in vivo, e.g., by biological fluids or enzymes, by a subject after administration into a pharmacologically active or more active form of the compound in order to produce the desired pharmacological effect. Prodrugs of a compound of Formula I can be prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that can be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp. 352–401; *Design of Prodrugs*, edited by H. Bundgaard, Elsevier Science, Amsterdam, 1985; *Design of Biopharmaceutical Properties through Prodrugs and Analogs*. Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

"Pharmacological effect" as used herein encompasses effects produced in the subject that achieve the intended purpose of a therapy. In one preferred embodiment, a pharmacological effect means that disorders or symptoms of the primary indications or primary indications itself of the subject being treated are prevented, alleviated, or reduced. For examples, a pharmacological effect would be one that results in the prevention or reduction of primary indications in a treated subject.

"Disease state" means any disease, condition, symptom, or indication.

"Treating" or "treatment" of a disease state includes:
(i) preventing the disease state, i.e., causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

"$\alpha_1$ adrenergic receptors", "$\alpha_{1A}$ adrenergic receptors" (previously known as "$\alpha_{1C}$ adrenergic receptors"), "$\alpha_{1B}$ adrenergic receptors", "$\alpha_{1D}$ adrenergic receptors" or "$\alpha_1$ adrenergic receptors", used interchangeably with "$\alpha_1$ adrenoceptors", "$\alpha_{1A}$ adrenoceptors" (previously known as "$\alpha_{1C}$ adrenoceptors receptors"), "$\alpha_{1B}$ adrenoceptors", "$\alpha_{1D}$ adrenoceptors" or "$\alpha_{1L}$ adrenoceptors", respectively, refers to a molecule conforming to the seven membrane-spanning G-protein receptors, which under physiologic conditions mediate various actions, for example, in the central and/or peripheral sympathetic nervous system through the binding of the catecholamines, epinephrine and norepinephrine. Examples of physiological effects mediated by "$\alpha_1$ adrenoceptors" include, but are not limited to, control of blood pressure, glycogenolysis, growth and hypertrophy of cardiac myocytes, contractility of the urinary tract, and the like.

The term "$\alpha_1$ adrenergic receptor subtype" used interchangeably with "$\alpha_1$ adrenoceptor subtype" refers to a distinct member of the class of $\alpha_1$ adrenoceptors, selected from the "$\alpha_{1A}$ (previously known as $\alpha_{1C}$), $\alpha_{1B}$, $\alpha_{1D}$, or $\alpha_{1L}$ receptors". The subtypes have been distinguished based on differential binding profiles of ligands, such as the agonist, oxymetazoline, and the antagonists, WB4101 and phentolamine. Furthermore, the genes encoding the $\alpha_{1A}$ (previously known as $\alpha_{1C}$), $\alpha_{1B}$, and $\alpha_{1D}$ subtypes have been isolated and cloned. The existence of an additional subtype, the $\alpha_{1L}$ adrenergic receptor subtype, has been proposed; however, the gene for the $\alpha_{1L}$ adrenergic receptor subtype has not yet been cloned.

The term "specific $\alpha_1$ adrenergic receptor" as used herein, refers to a distinct member of the group or class of adrenoceptors, which may be selected from the human $\alpha_{1A}$ (previously known as $\alpha_{1C}$), $\alpha_{1B}$, $\alpha_{1C}$, and $\alpha_{1L}$ adrenergic receptors. Preferred species from which may be derived or isolated $\alpha_1$ adrenergic receptor subtype polypeptides, genes encoding and $\alpha_1$ adrenergic receptor subtype, and/or cells, tissues and organs that express one or more $\alpha_1$ adrenergic receptor subtype, include human, bovine, rat, murine, porcine, and the like. A more preferred species is human.

"$\alpha_{1B}$ adrenergic receptor" means the specific $\alpha_1$ adrenoceptor expressed in numerous tissues, most notably in the liver, heart, and cerebral cortex. $\alpha_{1B}$ adrenoceptors are also present in areas of the spinal cord, which receive input from sympathetic neurons originating in the pontine micturition center, and are presumed to be involved in the regulation of bladder function.

"Agonist" means a molecule, such as a compound, a drug, an enzyme activator, or a hormone, that enhances the activity of another molecule or receptor site.

"Trauma" means any wound or injury. Trauma can produce, for example, acute and/or chronic pain, inflammatory pain, and neuropathic pain.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Disease states associated with the Central Nervous System (CNS)" or "CNS disease states" mean neurological and/or psychiatric changes in the CNS, e.g., brain and spinal cord, which manifest in a variety of symptoms. Examples of CNS disease states include, but are not limited to, migraine headache; cerebrovascular deficiency; psychoses including paranoia, schizophrenia, attention deficiency, and autism; obsessive/compulsive disorders including anorexia and bulimia; convulsive disorders including epilepsy and withdrawal from addictive substances; cognitive diseases including Parkinson's disease and dementia; and anxiety/depression disorders such as anticipatory anxiety (e.g., prior to surgery, dental work and the like), depression, mania seasonal affective disorder (SAD), and convulsions and anxiety caused by withdrawal from addictive substances such as opiates, benzodiazepines, nicotine, alcohol, cocaine, and other substances of abuse; and improper thermoregulation.

"Disease states associates with the gastrointestinal system (GI)" or "GI disease states" mean physiological changes in the alimentary tract. Examples of GI disease states include, but are not limited to, dyspepsia, gastric stasis, peptic ulcer, reflux esophagitis, bile reflux gastritis, pseudo-obstruction syndrome, diverticulitis, irritable bowel syndrome (IBS), inflammatory bowel disease, Crohn's disease, flatulence, biliary dysmotility, gastroparesis, retarded gastric emptying, chronic and acute diarrhea, diarrhea induced by cholera and carcinoid syndrome, and disturbed colonic motility. Other uses include short-term prokinesis to facilitate diagnostic radiology and intestinal intubation.

"Disease states associated with the cardiovascular system (CV)" or "CV disease states" mean a physiological or pathological alteration in the cardiovascular system, in particular, improper cardiac chronotropy or arrhythmia. Examples of CV disease states include, but are not limited to, bradyarrhythmia, tachyarrhythmia, supraventricular arrhythmia, atrial fibrillation, atrial flutter, or atrial tachycardia.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The terms "those defined above" and "those defined herein" when referring to a variable incorporates by reference the broad definition of the variable as well as preferred, more preferred and most preferred definitions, if any.

Nomenclature and Structures

In general, the nomenclature used in this Application is based on AUTONOM™ v. 4.0, a Beilstein Institute computerized system for the generation of IUPAC systematic nomenclature. Chemical structures shown herein are prepared using ISIS® v. 4.0. Any open valency appearing on a carbon, oxygen or nitrogen atom in the structures herein indicates the presence of a hydrogen.

Compounds

In one aspect, the present invention provides a compound of the formula:

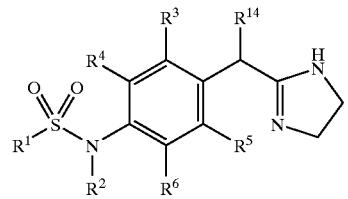

I a pharmaceutically acceptable salt or a prodrug thereof, wherein
  $R^1$ is alkyl, —$NR^7R^8$, where each of $R^7$ and $R^8$ is independently hydrogen or alkyl;
  $R^2$ is hydrogen or alkyl;
  each of $R^3$, $R^4$, $R^5$, and $R^6$ is independently hydrogen, halide, alkyl, —$OR^9$, where $R^9$ is hydrogen, alkyl, a hydroxy protecting group, or cycloalkylalkyl, —$SR^{10}$, where $R^{10}$ is hydrogen or alkyl, or —$NR^{11}R^{12}$, where each of $R^{11}$ and $R^{12}$ is independently hydrogen, alkyl, or a nitrogen protecting group, provided $R^3$, $R^4$, $R^5$, and $R^6$ are not all simultaneously alkyl; or $R^3$ and $R^4$ together with atoms to which they are attached to form heterocyclyl, heteroaryl, or cycloalkyl; and
  $R^{14}$ is hydrogen, lower alkyl, or —$OR^{15}$, where $R^{15}$ is hydrogen, lower alkyl, or a hydroxy protecting group.

It is to be understood that the scope of this invention encompasses not only the various isomers which may exist but also the various mixture of isomers which may be formed. Furthermore, the scope of the present invention also encompasses solvates and salts of Compounds of Formula I.

With respect to Compound of Formula I:
  Preferably, $R^1$ is alkyl. More preferably, $R^1$ is selected from the group consisting of methyl, ethyl, and isopropyl. Still more preferably, $R^1$ is methyl.
  Preferably, $R^2$ is hydrogen.
  Preferably, each of $R^3$, $R^4$, $R^5$, and $R^6$ is independently hydrogen, halide, alkyl, or —$OR^9$, where $R^9$ is hydrogen, alkyl, a hydroxy protecting group, or cycloalkylalkyl; or $R^3$ and $R^4$ together with atoms to which they are attached to form heterocyclyl, heteroaryl, or cycloalkyl.
  Preferably, $R^{14}$ is hydrogen, methyl or hydroxy. More preferably, $R^{14}$ is hydrogen.
  In one particular embodiment, at least one of $R^3$, $R^4$, $R^5$, and $R^6$ is alkyl, halide, or —$OR^9$, where $R^9$ is that defined herein. Preferably, at least one of $R^3$, $R^4$, $R^5$, and $R^6$ is chloro, bromo, fluoro, methoxy, ethoxy, methyl, and hydroxy. Alternatively, at least two of $R^3$, $R^4$, $R^5$, and $R^6$ are hydrogen Particularly preferred Compounds of Formula I include the following substituents on the phenyl moiety:

(a) $R^3$ is methoxy, and $R^4$, $R^5$, and $R^6$ are hydrogen;
(b) $R^3$ is methyl, $R^6$ is methoxy, and $R^4$ and $R^5$ are hydrogen;
(c) $R^3$ is methyl, $R^6$ is chloro, and $R^4$ and $R^5$ are hydrogen;
(d) $R^3$ is chloro, $R^4$ is methoxy, and $R^5$ and $R^6$ are hydrogen;
(e) $R^3$ is methyl, $R^4$ is chloro, and $R^5$ and $R^6$ are hydrogen;
(f) $R^3$ is methyl, $R^4$ is methoxy, and $R^5$ and $R^6$ are hydrogen;
(g) $R^4$ is chloro, and $R^3$, $R^5$ and $R^6$ are hydrogen;
(h) $R^4$ is methoxy, and $R^3$, $R^5$, and $R^6$ are hydrogen;
(i) $R^3$ is methyl, $R^6$ is bromo, and $R^4$ and $R^5$ are hydrogen;
(j) $R^3$ is bromo, $R^4$ is methoxy, and $R^5$ and $R^6$ are hydrogen;
(k) $R^3$ is methyl, $R^4$ is bromo, and $R^5$ and $R^6$ are hydrogen;
(l) $R^4$ is bromo, and $R^3$, $R^5$ and $R^6$ are hydrogen; and
(m) $R^3$ is ethoxy and $R^4$, $R^5$ and $R^6$ are hydrogen.

In another embodiment, $R^3$ and $R^4$ together with atoms to which they are attached to form furanyl, dihydrofuranyl, pyrrolyl, or phenyl group. Preferably, $R^3$ and $R^4$ together with atoms to which they are attached to form furanyl or dihydrofuranyl. The following Compounds of Formula I in which $R^3$ and $R^4$ together with atoms to which they are attached to form furanyl or dihydrofuranyl, respectively, are particularly preferred:

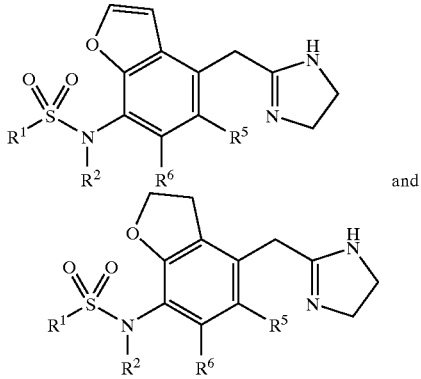

and

Still further, combinations of the preferred groups described herein will form other preferred embodiments. For example, in one group of particularly preferred embodiments $R^1$ is methyl, $R^2$ is hydrogen and at least one of $R^3$, $R^4$, $R^5$, and $R^6$ is alkyl, halide, or $-OR^{10}$, where $R^{10}$ is that defined herein. In this manner, a variety of preferred compounds are embodied within the present invention.

Some of the representative Compounds of Formula I are shown in Table 1 below: Table of Representative Compounds of Formula I:

TABLE 1

| | Name (Autonom ®) | Example | Structure |
|---|---|---|---|
| 1 | N-[4-(4,5-Dihydro-1H-imidazol-2-ylmethyl)-phenyl]-methanesulfonamide; | 2 | 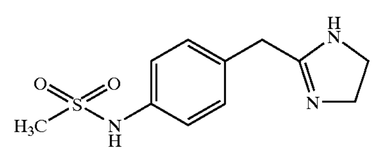 |
| 2 | N-[4-(4,5-Dihydro-1H-imidazol-2-ylmethyl)-2-methoxy-phenyl]-methanesulfonamide; | 2 | 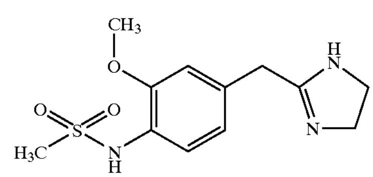 |
| 3 | N-[4-(4,5-Dihydro-1H-imidazol-2-ylmethyl)-2-methyl-phenyl]-methanesulfonamide | 2 | 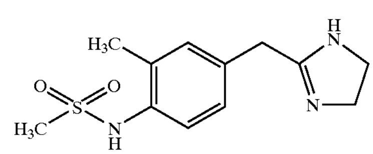 |
| 4 | N-[2-Chloro-4-(4,5-dihydro-1H-imidazol-2-ylmethyl)-phenyl]-methanesulfonamide | 3 | 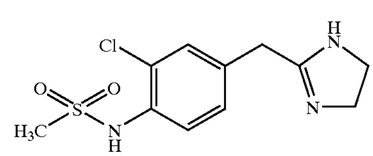 |

TABLE 1-continued

| | Name (Autonom ®) | Example | Structure |
|---|---|---|---|
| 5 | N-[4-(4,5-Dihydro-1H-imidazol-2-ylmethyl)-2-hydroxy-phenyl]-methanesulfonamide | 2 | 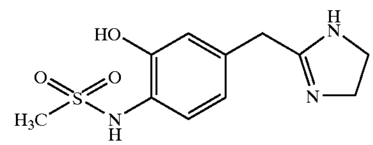 |
| 6 | N-[4-(4,5-Dihydro-1H-imidazol-2-ylmethyl)-3-methoxy-phenyl]-methanesulfonamide; | 2 | 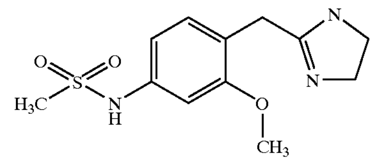 |
| 7 | N-[4-(4,5-Dihydro-1H-imidazol-2-ylmethyl)-2-methoxy-3-methyl-phenyl]-methanesulfonamide | 2 | 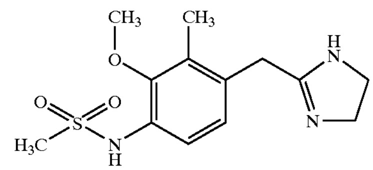 |
| 8 | N-[4-(4,5-Dihydro-1H-imidazol-2-ylmethyl)-benzofuran-7-yl]-methanesulfonamide | 1 | 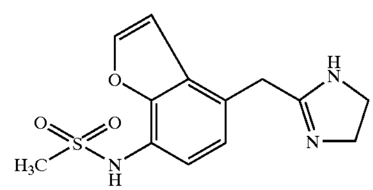 |
| 9 | N-[3-Chloro-4-(4,5-dihydro-1H-imidazol-2-ylmethyl)-phenyl]-methanesulfonamide | 1 | 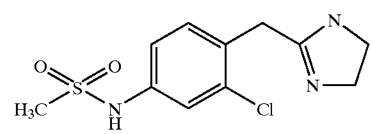 |
| 10 | N-[4-(4,5-Dihydro-1H-imidazol-2-ylmethyl)-3-hydroxy-phenyl]-methanesulfonamide | 2 | 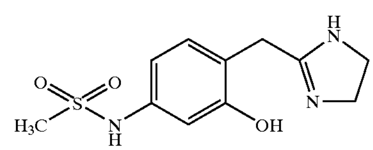 |
| 11 | N-[4-(4,5-Dihydro-1H-imidazol-2-ylmethyl)-2,3-dihydro-benzofuran-7-yl]-methanesulfonamide | 1 | 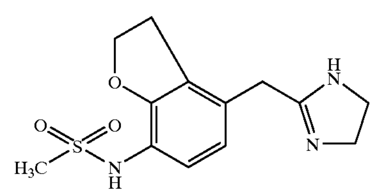 |
| 12 | N-{4-[(4,5-Dihydro-1H-imidazol-2-yl)-hydroxy-methyl]-2-methoxy-phenyl}-methanesulfonamide; | 4 | 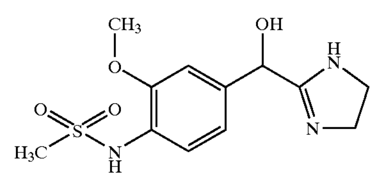 |
| 13 | Ethanesulfonic acid [2-chloro-4-(4,5-dihydro-1H-imidazol-2-ylmethyl)-phenyl]-amide | 1 | 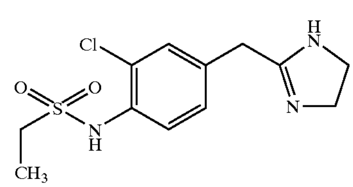 |

TABLE 1-continued

| | Name (Autonom ®) | Example | Structure |
|---|---|---|---|
| 14 | Propane-2-sulfonic acid [2-chloro-4-(4,5-dihydro-1H-imidazol-2-ylmethyl)-phenyl]-amide | 1 | 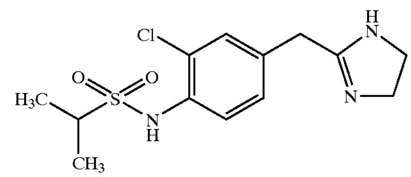 |
| 15 | N-[4-(4,5-Dihydro-1H-imidazol-2-ylmethyl)-5-fluoro-2-methoxy-phenyl]-methanesulfonamide | 4 | 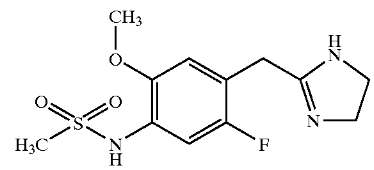 |
| 16 | N-[4-(4,5-Dihydro-1H-imidazol-2-ylmethyl)-2-methoxy-5-methyl-phenyl]-methanesulfonamide | 4 | 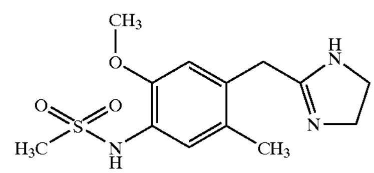 |
| 17 | N-[2-Chloro-4-(4,5-dihydro-1H-imidazol-2-ylmethyl)-3-methyl-phenyl]-methanesulfonamide | 4 | 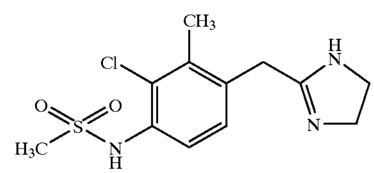 |
| 18 | Ethanesulfonic acid [4-(4,5-dihydro-1H-imidazol-2-ylmethyl)-2-methoxy-3-methyl-phenyl]-amide | 2 | 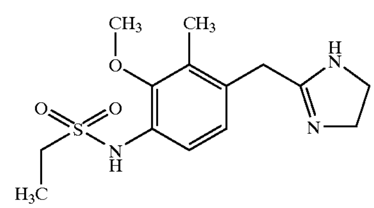 |
| 19 | N-[2-Chloro-4-(4,5-dihydro-1H-imidazol-2-ylmethyl)-6-methyl-phenyl]-methanesulfonamide | 1 | 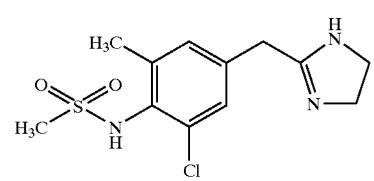 |
| 20 | N-[2-Chloro-4-(4,5-dihydro-1H-imidazol-2-ylmethyl)-6-methoxy-phenyl]-methanesulfonamide | 4 | 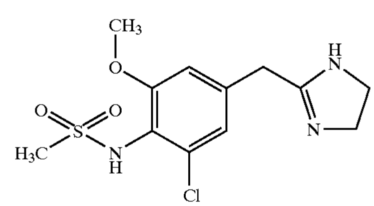 |
| 21 | N-[2-Chloro-4-(4,5-dihydro-1H-imidazol-2-ylmethyl)-5-methoxy-phenyl]-methanesulfonamide | 1 | 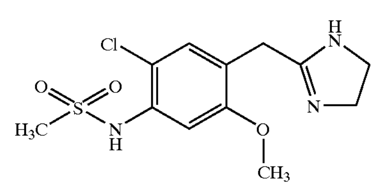 |

TABLE 1-continued

| Name (Autonom ®) | Example |
|---|---|
| 22  N-[4-(4,5-Dihydro-1H-imidazol-2-ylmethyl)-2,5-dimethoxy-phenyl]-methanesulfonamide | 4 |
| 23  N-[4-(4,5-Dihydro-1H-imidazol-2-ylmethyl)-2-methoxy-5-methyl-phenyl]-N-methyl-methanesulfonamide | 4 |
| 24  N-[3-Chloro-4-(4,5-dihydro-1H-imidazol-2-ylmethyl)-2-methoxy-phenyl]-methanesulfonamide | 4 |
| 25  N-[5-Chloro-4-(4,5-dihydro-1H-imidazol-2-ylmethyl)-2-methoxy-phenyl]-methanesulfonamide | 4 |
| 26  N-[2-Chloro-4-(4,5-dihydro-1H-imidazol-2-ylmethyl)-5-methyl-phenyl]-methanesulfonamide | 4 |
| 27  N-[4-(4,5-Dihydro-1H-imidazol-2-ylmethyl)-2-methoxy-6-methyl-phenyl]-methanesulfonamide | 4 |
| 28  N-{4-1-[(4,5-Dihydro-1H-imidazol-2-yl)-ethyl]-2-methoxy-phenyl}-methanesulfonamide | 4 |
| 29  N-[2-Ethoxy-4-(4,5-dihydro-1H-imidazol-2-ylmethyl)-phenyl]-methanesulfonamide | 4 |

TABLE 1-continued

| | Name (Autonom ®) | Example | Structure |
|---|---|---|---|
| 30 | Ethanesulfonic acid [4-(4,5-dihydro-1H-imidazol-2-ylmethyl)-2-methoxy-phenyl]-amide | 4 | 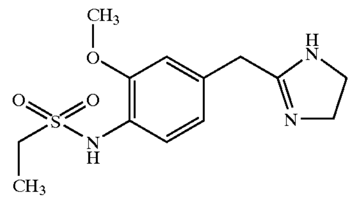 |
| 31 | N-[3-Chloro-2-hydroxy-4-(4,5-dihydro-1H-imidazol-2-ylmethyl)-phenyl]-methanesulfonamide | 4 | 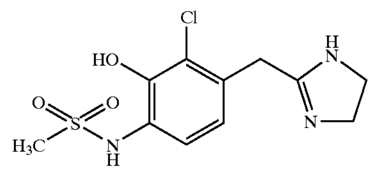 |
| 32 | N-[2-Bromo-4-(4,5-dihydro-1H-imidazol-2-ylmethyl)-3-methyl-phenyl]-methanesulfonamide | 4 | 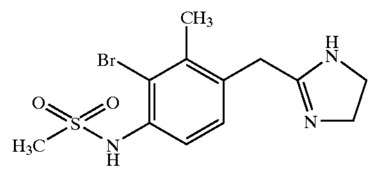 |
| 33 | N-[2-Bromo-4-(4,5-dihydro-1H-imidazol-2-ylmethyl)-phenyl]-methanesulfonamide | 4 | 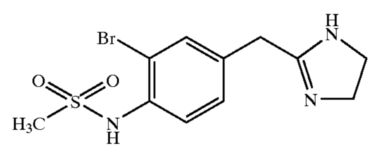 |
| 34 | Ethanesulfonic acid [2-bromo-4-(4,5-dihydro-1H-imidazol-2-ylmethyl)-3-methyl-phenyl]-amide | 4 | 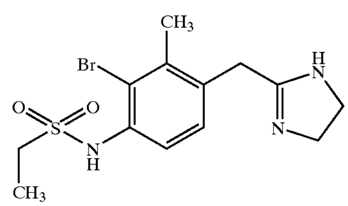 |
| 35 | Ethanesulfonic acid [2-chloro-4-(4,5-dihydro-1H-imidazol-2-ylmethyl)-3-methyl-phenyl]-amide | 4 | 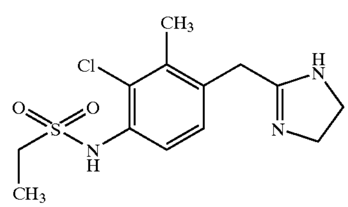 |
| 36 | N-[4-(4,5-Dihydro-1H-imidazol-2-ylmethyl)-3-ethoxy-phenyl]-methanesulfonamide | 4 | 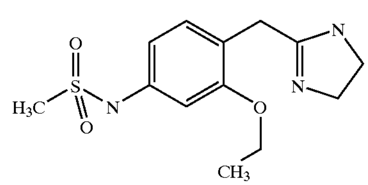 |
| 37 | N-[3-Cyclopropylmethoxy-4-(4,5-dihydro-1H-imidazol-2-ylmethyl)-phenyl]-methanesulfonamide | 4 | 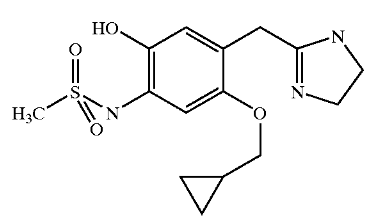 |

TABLE 1-continued

| | Name (Autonom ®) | Example | Structure |
|---|---|---|---|
| 38 | N-[2-Chloro-4-(4,5-dihydro-1H-imidazol-2-ylmethyl)-5-fluoro-phenyl]-methanesulfonamide | 4 | 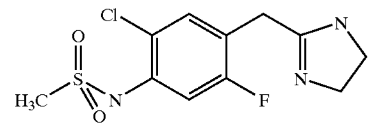 |
| 39 | N-[4-(4,5-Dihydro-1H-imidazol-2-ylmethyl)-2-hydroxy-5-methoxy-phenyl]-methanesulfonamide | 4 | 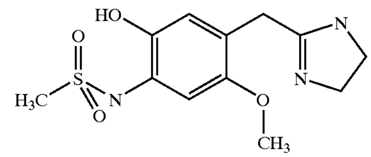 |
| 40 | N-[4-(4,5-Dihydro-1H-imidazol-2-ylmethyl)-2-fluoro-phenyl]-methanesulfonamide | 4 | 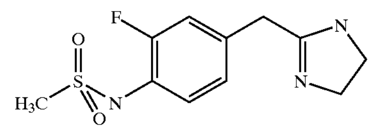 |

General Synthetic Reaction Schemes

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In one embodiment, Compounds of Formula I are prepared by reacting a nitrile compound of the formula:

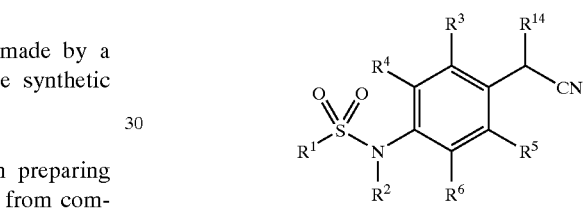

II with ethylene diamine (i.e., $H_2N-CH_2-CH_2-NH_2$) to produce the imidazolin-2-ylmethyl-substituted aromatic compound of Formula I.

Formation of the imidazoline moiety can be achieved using a variety of reaction conditions. In one embodiment, the nitrile Compound of Formula II is dissolved or suspended in a protic organic solvent, such as an alcohol (e.g., anhydrous ethanol), and an acid, e.g., hydrogen chloride gas, is added. Typically, the addition of acid is conducted at about 0° C. to about 5° C. The reaction mixture is then kept at the low temperature for about 10 hours to about 48 hours, preferably about 24 hours, after which the reaction mixture is concentrated under reduced pressure. The resulting residue, which is typically a solid, is re-dissolved in an anhydrous protic solvent, e.g., methanol, and ethylene diamine added to the solution. Typically, about 1 equivalent to a slight excess, e.g., 1.2 equivalents, of ethylene diamine is added. The resulting reaction mixture is then heated to reflux. The reaction time varies depending on a variety of factors, such as concentration of each reagents, exact nature of the reagents, etc. Typically, however, the reaction mixture is heated for from about 10 hours to about 48 hours, preferably for about 24 hours, to afford the imidazolin-2-ylmethyl substituted arylalkylsulfonamide of Formula I.

Alternatively, the imidazoline moiety can be formed by microwaving a mixture of the nitrile Compound of Formula II, ethylene diamine, and a small amount of carbon disulfide. For example, using a Smith creator™ microwave reaction apparatus. In this embodiment, typically ethylene diamine serves both as a solvent and a reagent. Thus, generally an excess amount of ethylene diamine is used, e.g., from about 10 to about 50 equivalents or more. Typical microwave temperature is from about 100° C. to about 250° C., preferably about 130° C. to about 170° C., and more preferably about 140° C. The reaction time can vary depending on a variety of factors, such as those mentioned above. However, typical reaction time is from about 10 minutes to about 60 minutes, preferably about 20 minutes to about 40 minutes, and more preferably about 30 minutes.

The nitrile Compound of Formula II can be readily prepared from a variety of starting materials. In one particular embodiment, the nitrile Compound of Formula II is synthesized from a reaction between a corresponding benzaldehyde of the formula:

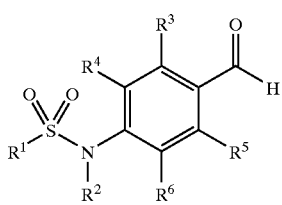

and an isocyanide. Suitable isocyanides for the conversion of the aldehyde functional group to a nitrile group include tosylmethyl isocyanide (TosMIC) and other isocyanides known to one skilled in the art. The reaction generally involves adding the isocyanide to a base, e.g., a hydroxide or an alkoxide, such as potassium tert-butoxide, at a low temperature. The reaction temperature is generally kept at from about −78° C. to about −20° C., preferably from about −65° C. to about −60° C. Conventionally, an excess amount of the base is used, typically about 2 equivalents to about 5 equivalents, preferably about 2.5 equivalents. The reaction between the base and the isocyanide is conveniently carried out in an inert organic solvent, such as ether, e.g., ethylene glycol dimethyl ether.

After reacting the isocyanide with the base, the benzaldehyde of Formula III is added to the reaction mixture to produce the nitrile Compound of Formula II. This stage of the reaction often involves stirring the reaction mixture at a low temperature, typically about −60° C. or less, for about an hour and adding a protic solvent, such as methanol. The resulting mixture is then heated to reflux for from about 10 minutes to 60 minutes, preferably about 20 minutes, and further stirred at room temperature for additional about 10 to 20 hours, typically about 16 hours.

The benzaldehyde of Formula III can be readily obtained using a variety of synthetic methods including those shown in Scheme I below and in the Examples section.

Scheme I

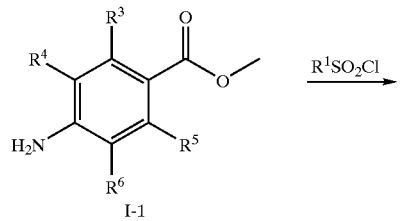

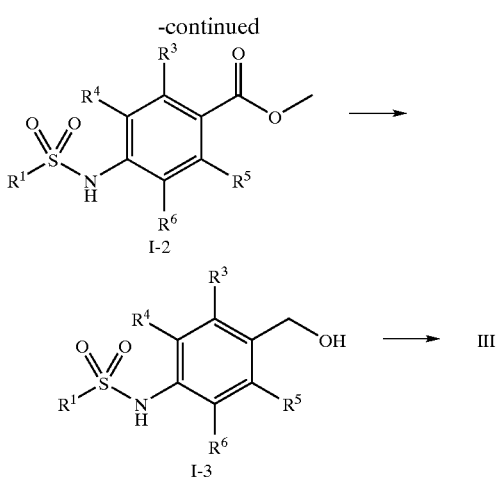

As shown in Scheme I, the ester I-1, which is commercially available or can be readily obtained from a commercially available material, is sulfonylated with an activated sulfonyl compound, e.g., alkylsulfonyl chloride, to produce a sulfonamide I-2. Typically, this sulfonylation reaction involves adding a sulfonyl chloride to a solution of the ester I-1 in an inert organic solvent, e.g., dichloromethane, at room temperature or lower.

The ester group of the sulfonamide I-2 is then reduced with a reducing agent to produce an alcohol I-3. Suitable reducing agents and reaction conditions for producing the benzyl alcohol I-3 are well known to one skilled in the art. For example, one embodiment involves adding diisobutylaluminum hydride (DIBAL) to a 0° C. solution of the sulfonamide I-2 in tetrahydrofuran (THF).

Oxidation of the benzyl alcohol I-3 then affords the benzaldehyde of Formula III. Suitable oxidizing agents and reaction conditions for producing the benzaldehyde of Formula III are well known to one skilled in the art. For example, the benzyl alcohol I-3 can be oxidized using pyridinium chlorochromate (PCC) in dichloromethane at room temperature to produce the benzaldehyde of Formula III.

Other methods for producing the nitrile Compound of Formula II include those shown in Scheme II below and in the Examples section.

Scheme II

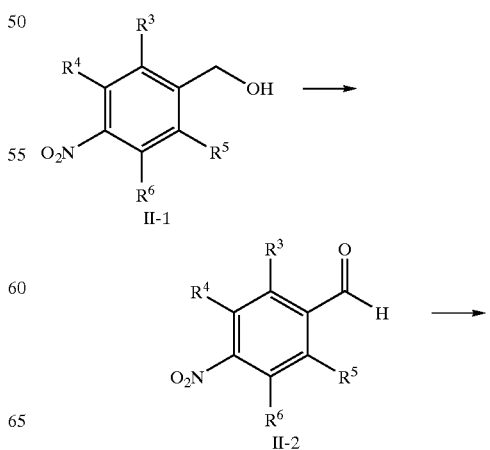

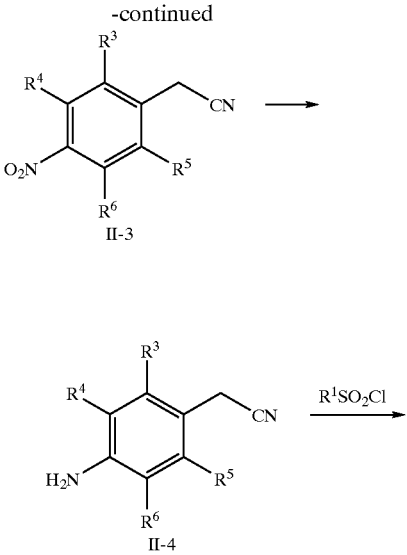

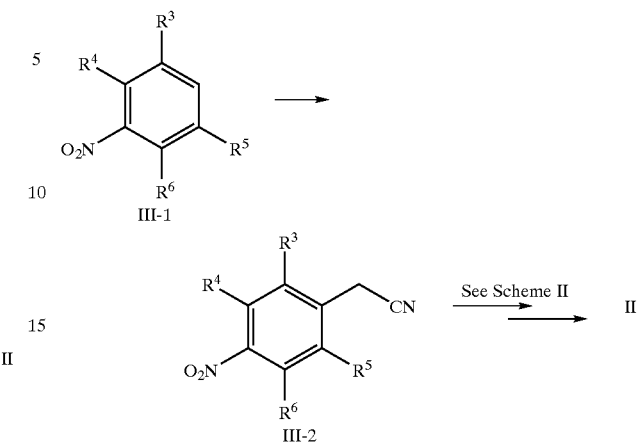

Scheme III

In this embodiment, the nitrile group is introduced prior to converting the nitro group to a sulfonamido group. A benzyl alcohol II-1 is commercially available or can be readily synthesized from a commercially available corresponding ester or a carboxylic acid by reduction. Such reduction conditions are similar to those described above in Scheme I for the reduction of the ester group of the sulfonamide of Formula I-2. The benzyl alcohol II-1 is then oxidized, for example, using an oxidizing agent and reaction conditions similar to those described above in Scheme I for oxidizing the benzyl alcohol of Formula I-3. The benzaldehyde of Formula II-2 is then converted to a benzyl nitrile of Formula II-3 using conditions similar to those described above for transformation of the benzaldehyde of Formula III to the nitrile Compound of Formula-II.

The nitro group of benzyl nitrile of Formula II-3 is then reduced to provide an aniline of Formula II-4. Reduction of a nitro group on an aromatic ring is well known to one skilled in the art. For example, the nitro group of benzyl nitrile of Formula II-3 can be reduced by hydrogenation in the presence of a catalyst. Suitable hydrogenation catalyst include a variety of well known transition metal catalysts, including palladium on carbon catalyst. Typically, the hydrogenation reaction is conducted in an alcoholic solvent, e.g., methanol or ethanol, under elevated pressure, e.g., about 45 psi. The nitro group can also be converted to an amino group using a reducing agent, such as stannous chloride ($SnCl_2$) and other nitro group reducing agents known to one skilled in the art. The aniline of Formula II-4 is then sulfonylated to produce the nitrile Compound of Formula II. The sulfonylation reaction conditions are similar to those described above in Scheme I for the conversion of the ester of Formula I-1 to the sulfonamide of Formula I-2.

Still other methods for producing the nitrile Compound of Formula II include those shown in Scheme III below and in the Examples section.

In this embodiment, a reaction between the nitrophenyl compound of Formula III-1 and an acetonitrile derivative provides a nitrobenzonitrile compound of Formula III-2. Suitable acetonitrile derivatives include phenylthioacetonitrile, chloroacetonitrile, thiomethylacetonitrile, phenoxyacetonitrile, phenylsulfonyl acetonitrile, methylsulfonyl acetonitrile, dimethyldithiocarbamoyl acetonitrile, and other acetonitrile derivatives known to one skilled in the art. See, for example, Winiarski, J. Org. Chem., 1980, 45, 1534 and Winiarski, J. Org. Chem., 1984, 49, 1494, both of which are incorporated herein be reference in their entirety. Typically, a mixture of the nitrophenyl compound of Formula III-1 and the acetonitrile derivative is added to a suspension of a base, e.g., a hydroxide or an alkoxide, in a relatively polar organic solvent, such as dimethylsulfoxide (DMSO). The reaction temperature is generally maintained at below 40° C., preferably below 30° C. While the reaction time can vary depending on many factors, including the concentration, reaction temperature, substituents on the phenyl ring, etc., generally the reaction time ranges from about 30 minutes to about 5 hours, preferably about 1 hour, at room temperature. The nitrobenzonitrile compound of Formula III-2 is then converted to the nitrile Compound of Formula II using procedures similar to those described in Scheme II.

In another embodiment, Compounds of Formula I can be produced from a reaction between an ester compound of the formula:

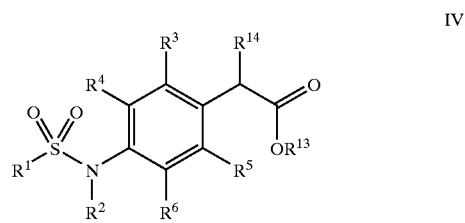

IV with ethylene diamine in the presence of a trialkylaluminum, such as trimethylaluminum and triethylaluminum. See, for example, Gunter, J. Org. Chem., 1981, 46, 2824, which is incorporated herein by reference in its entirety.

The ester Compound of Formula IV can be prepared by a variety of methods. In one particular embodiment, the ester Compound of Formula IV is produced using methods shown in Scheme IV below and discussed in detail in the Examples section.

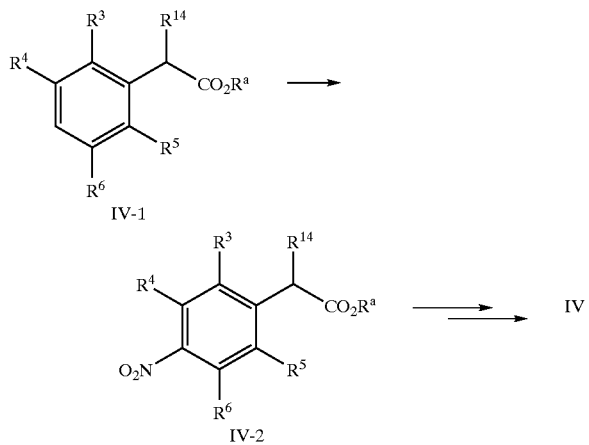

Scheme IV

Thus, nitration of the ester IV-1 under conventional aromatic nitration conditions provides nitro-ester compound of Formula IV-2. The nitro group is then reduced and sulfonylated using conditions similar to those described above to produce the ester Compound of Formula IV.

The amino group or the sulfonamido group in any of the appropriate intermediates described above can be alkylated to produce the corresponding Compound of Formula I, where $R^2$ is alkyl. Such an alkylation can be carried out neat at about 0° C. to about 25° C., typically at about 10° C. to about 150° C., and preferably at about 20° C. to about 60° C. While the alkylation reaction time varies depending on a various factors discussed above, the alkylation reaction time is generally from about 1 to about 24 hours.

The alkylation is typically carried out in a suitable inert organic solvent (e.g., acetonitrile, methylsulfoxide (DMSO), N,N-dimethylformamide (DMF), N-methylpyrrolidione (NMP), benzene, toluene, any appropriate mixture of suitable solvents, etc., preferably acetonitrile or DMSO) in the presence of a base. Suitable bases for alkylation are well known to one skilled in the art and include, sodium carbonate, potassium carbonate, cesium carbonate, 2,4,6-trimethylpyridine, triethylamine, N,N-diisopropylethylamine, and sodium hydride, etc. Preferably, the base is sodium carbonate, triethylamine, or N,N-diisopropylethylamine.

General Utility

The compounds of the present invention have selective $\alpha_{1A}$- or $\alpha_{1L}$-adrenergic activity and as such are useful in the treatment of various disease states, such as urinary incontinence; nasal congestion; sexual dysfunction, such as ejaculation disorders and priapism; CNS disorders such as depression, anxiety, dementia, senility, Alzheimer's, deficiencies in attentiveness and cognition, and eating disorders such as obesity, bulimia, and anorexia.

Urinary incontinence (UI) is a condition defined as the involuntary loss of urine to such an extent as to become a hygienic or social concern to the patient. Involuntary loss of urine occurs when pressure inside the bladder exceeds retentive pressure of the urethral sphincters (intraurethral pressure). Four major types of urinary incontinence have been defined based on symptoms, signs and condition: stress, urge, overflow and functional incontinence.

Stress urinary incontinence (SUI) is the involuntary loss of urine during coughing, sneezing, laughing, or other physical activities. The present methods to treat SUI include physiotherapy and surgery. Treatment with pharmaceutical agents is limited to the use of non selective-adrenergic agonists like phenylproanolane and midodrine. The rationale for the use of adrenergic agonists for the treatment of SUI is based on physiological data indicating an abundant noradrenergic input to smooth muscle of the urethra.

Urge incontinence (detrusor instability) is the involuntary loss of urine associated with a strong urge to void. This type of incontinence is the result of either an overactive or hypersensitive detrusor muscle. The patient with detrusor overactivity experiences inappropriate detrusor contractions and increases in intravesical pressure during bladder filling. Detrusor instability resulting from a hypersensitive detrusor (detrusor hyperreflexia) is most often associated with a neurological disorder.

Overflow incontinence is an involuntary loss of urine resulting from a weak detrusor or from the failure of the detrusor to transmit appropriate signals (sensory) when the bladder is full. Overflow incontinent episodes are characterized by frequent or continuous dribbling of urine and incomplete or unsuccessful voiding.

Functional incontinence, in contrast to the types of incontinence described above, is not defined by an underlying physiological dysfunction in the bladder or urethra. This type of incontinence includes the involuntary loss of urine resulting from such factors as decreased mobility, medications (e.g., diuretics, muscarinic agents, or alpha-1 adrenoceptor antagonists), or psychiatric problems such as depression or cognitive impairment.

The compounds of this invention are also particularly useful for the treatment of nasal congestion associated with allergies, colds, and other nasal disorders, as well as the sequelae of congestion of the mucous membranes (for example, sinusitis and otitis media) with less or no undesired side effects.

These and other therapeutic uses are described, for example, in Goodman & Gilman's, The Pharmacological Basis of Therapeutics, ninth edition, McGraw-Hill, New York, 1996, Chapter 26:601–616; and Coleman, R. A., Pharmacological Reviews, 1994, 46:205–229.

Testing

General Strategy for Identifying $\alpha_{1A/L}$-adrenoceptor Agonists:
In Vitro:

The activity of potential $\alpha_{1A/L}$ activity in vitro was determined by evaluating the potency and relative intrinsic activity (relative to norepinephrine or phenylephrine) of standard and novel compounds using fluorescent dye determination of intracellular calcium concentrations.
In Vivo:

Standard and novel compounds which selectively stimulated CHO—K1 cells expressing the $\alpha_{1A}$-adrenoceptor (clone 13 were subsequently evaluated in vivo in anesthetized female rabbits to assess urethral activity relative to diastolic blood pressure effects. Compounds with the desired activity in anesthetized rabbits were evaluated in conscious female rabbits instrumented with telemetry to measure diastolic blood pressure and a strain-gage transducer to measure urethral tension.

Administration and Pharmaceutical Composition

Another aspect of the present invention provides a pharmaceutical composition comprising a Compound of Formula I and a pharmaceutically acceptable carrier. Pharmaceutical compositions of the present invention can also include other therapeutic and/or prophylactic ingredients.

In general, the compounds of the present invention are administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Example 5.

EXAMPLES

The following preparations and examples are given to enable those skilled in the art to more clearly understand and to practice the present invention. They should not be considered as limiting the scope of the invention, but merely as being illustrative and representative thereof.

Example 1

This example illustrates a method for producing Compounds of Formula I using the synthetic scheme outlined below:

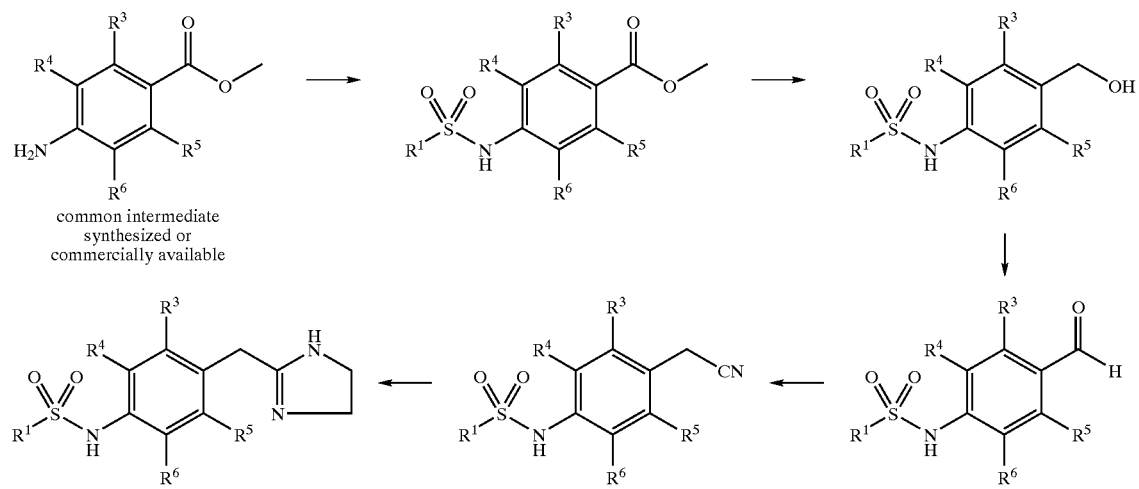

common intermediate synthesized or commercially available

Step 1

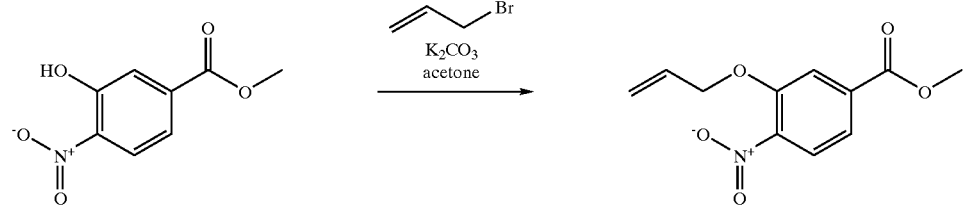

To a solution of 3-hydroxy-4-nitro-benzoic acid methyl ester (50.0 g, 253.6 mmol) in acetone (1 L) was added potassium carbonate (105.0 gram, 759.7 mmol) and allyl bromide (44.0 mL, 508.4 mmol). The reaction mixture was heated to reflux overnight and the insoluble material was removed by filtration. The filtrate was concentrated under reduced pressure to give 3-allyloxy-4-nitro-benzoic acid methyl ester as solid (59.4 g, 98.8%). $^1$H NMR (CDCl$_3$) δ3.96 (s, 3H), 4.75 (dt, 2H, J=5.0 Hz, 1.6 Hz), 5.36 (ddt, 1H, J=10.6 Hz, 1.4 Hz, 1.4 Hz), 5.50 (ddt, 1H, J=17.2 Hz, 1.6 Hz, 1.6 Hz), 6.05 (ddt, 1H, J=17.3 Hz, 10.6 Hz, 5.0 Hz), 7.69 (dd, 1H, J=8.33 Hz, 1.58 Hz), 7.75 (d, 1H, J=1.55 Hz), 7.83 (d, 1H, J=8.34 Hz).

Step 2

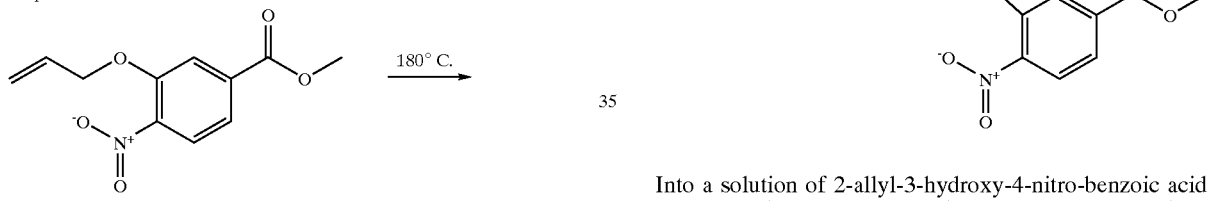

3-Allyloxy-4-nitro-benzoic acid methyl ester (58.1 g 245.0 mmol) was heated between 185° C. and 195° C. for nineteen hours and cooled to room temperature. The mixture was purified by flash column chromatography over silica gel eluting with 8% ethyl acetate in hexane to give 2-allyl-3-hydroxy-4-nitro-benzoic acid methyl ester (35.2 g, 60.6%) as a yellow oil. $^1$H NMR (CDCl$_3$) δ3.79 (dt, 2H, J=6.3 Hz, 1.5 Hz), 3.93 (s, 3H), 5.03–5.10 (m, 2H), 5.97 (ddt, 1H, J=16.8 Hz, 10.5 Hz, 6.2 Hz), 7.35 (d, 1H, J=8.9 Hz), 8.04 (d, 1H, J=8.9 Hz), 11.07 (s, 1H).

Step 3

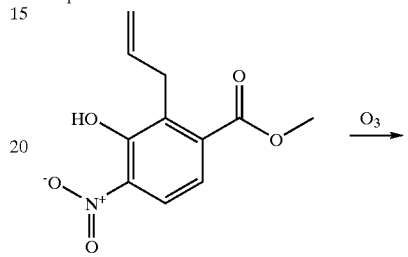

Into a solution of 2-allyl-3-hydroxy-4-nitro-benzoic acid methyl ester (6.11 g 25.6 mmol) in dichloromethane (100 mL) and methanol (10 mL) at −78° C. was bubbled with ozone for 40 minutes. After stirring for another 20 min at −70° C., a stream of nitrogen gas was passed through the reaction mixture. Dimethyl sulfide (5 mL, 68.1 mmol) was added at −78° C. The reaction solution was allowed to warm up gradually to room temperature overnight. The reaction mixture was partitioned between dichloromethane and water. The aqueous layer was further extracted twice with dichloromethane. The organic extract was washed with brine, dried (anhydrous sodium sulfate), and concentrated under reduced pressure to give 2-hydroxy-7-nitro-2,3-dihydro-benzofuran-4-carboxylic acid methyl ester as a yellow solid (6.0 g). $^1$H NMR (CDCl$_3$) δ: 3.51–3.74 (m, 2H), 3.96 (s, 3H), 6.43 (dd, 1H, J=6.4 Hz, 2.6 Hz), 7.63 (d, 1H, J=8.8), 8.01 (d, 1H, J=8.9 Hz).

Step 4

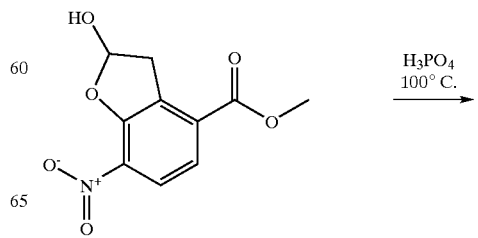

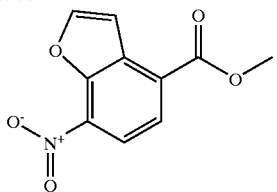

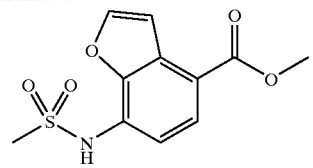

2-Hydroxy-7-nitro-2,3-dihydro-benzofuran-4-carboxylic acid methyl ester prepared above was heated in phosphoric acid (60 mL) at 100° C. for one hour. The reaction mixture was poured into ice water and the aqueous solution was extracted with ethyl acetate. The organic phase was washed with brine, dried (anhydrous sodium sulfate) and concentrated under reduced pressure. The residue was purified by flash column chromatography over silica gel eluting with 15% ethyl acetate in hexane to give 7-nitro-benzofuran-4-carboxylic acid methyl ester as solid (2.3 g, 40%). $^1$H (CDCl$_3$) δ: 4.04 (s, 3H), 7.54 (d, 1H, J=2.0 Hz), 7.95 (d, 1H, J=1.9 Hz), 8.07 (d, 1H, J=8.5 Hz), 8.17 (d, 1H, J=8.5 Hz).

To a solution of 7-amino-benzofuran-4-carboxylic acid methyl ester (6.14 g, 32.1 mmol) and pyridine (13.69 g, 173 mmole) in dichloromethane (100 mL) was added methanesulfonyl chloride (2.8 mL, 36.2 mmol). The reaction mixture was stirred at room temperature under nitrogen for 72 hours. The solvent was removed under reduced pressure and the residue partitioned between dichloromethane and 1 N hydrochloric acid. The organic extract was dried (anhydrous sodium sulfate) and concentrated. The residue was purified by flash column chromatography over silica gel eluting with 20 to 30% ethyl acetate in hexane to give 7-methanesulfonyl-amino-benzofuran-4-carboxylic acid methyl ester (7.73 g, 89%) as a solid. $^1$H NMR (CDCl$_3$) δ: 3.15 (s, 3H), 3.98 (s, 3H), 7.43 (d, 1H, J=2.2 Hz), 7.50 (d, 1H, J=8.4 Hz), 7.74 (d, 1H, J=2.1 Hz), 8.00 (d, 1H, J=8.3 Hz).

Step 5

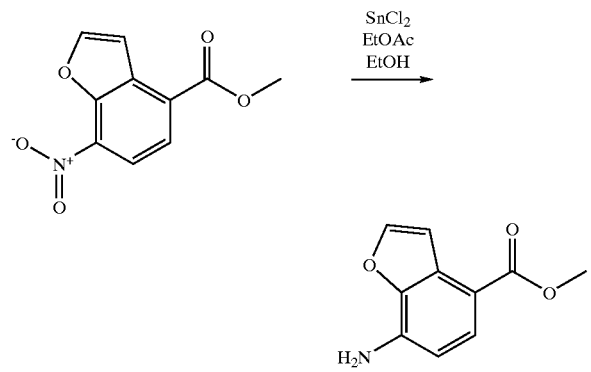

Step 7

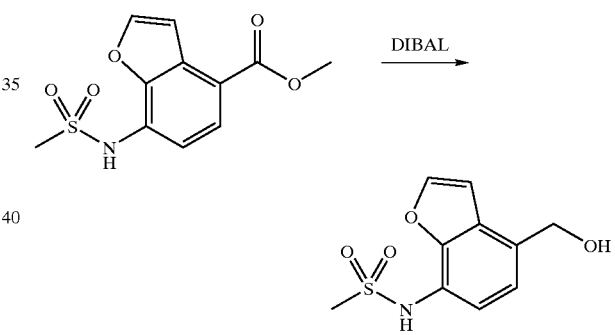

Tin (II) chloride dihydrate (15.0 g, 66.5 mmol) was added to a suspension of 7-nitro-benzofuran-4-carboxylic acid methyl ester (4.82 g, 21.8 mmol) in ethyl acetate (80 mL) and ethanol (80 mL). The reaction mixture was stirred at room temperature for four days then partitioned between ethyl acetate and saturated aqueous solution of potassium carbonate. The organic extract was washed with brine, dried (anhydrous sodium sulfate) and concentrated under reduced pressure. The residue was purified by flash column chromatography over silica gel eluting with 30% ethyl acetate in hexane give 7-amino-benzofuran-4-carboxylic acid methyl ester (3.67 g, 88%). $^1$H NMR (CDCl$_3$) δ: 3.92 (s, 3H), 6.60 (d, 1H, J=8.2 Hz), 7.34 (d, 1H, J=2.1 Hz), 7.67 (d, 1H, J=2.1 Hz), 7.84 (d, 1H, J=8.2 Hz).

Step 6

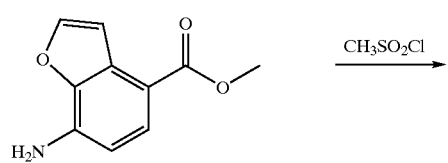

To a solution of 7-methanesulfonylamino-benzofuran-4-carboxylic acid methyl ester (6.42 g, 23.8 mmole) in anhydrous tetrahydrofuran (155 mL) was added a solution of diisobutylaluminum hydride (1.5M solution in toluene, 80 mL, 120 mmole) slowly at 0° C. under nitrogen. The ice bath was removed and the reaction mixture was stirred at room temperature for three hours. Methanol (30 mL) was added slowly at 0° C. The reaction mixture was partitioned between ethyl acetate and 0.5 N hydrochloric acid. The organic extract was washed with brine, dried (anhydrous sodium sulfate), and concentrated under reduced pressure. The residue was purified by flash column chromatography over silica gel eluting with 50 to 80% ethyl acetate in hexane to give N-(4-Hydroxymethyl-benzofuran-7-yl)-methanesulfonamide as a solid (5.64 g, 98%). $^1$H NMR (DMSO-d$_6$) δ: 3.07 (s, 3H), 4.73 (d, 2H, J=5.70 Hz), 5.30 (t, 1H J=5.7 Hz), 7.10 (d, 1H, J=2.2 Hz), 7.21 (s, 2H), 8.05 (d, 1H, J=2.2 Hz), 9.78 (s, 1H). M−H 240.

Step 8

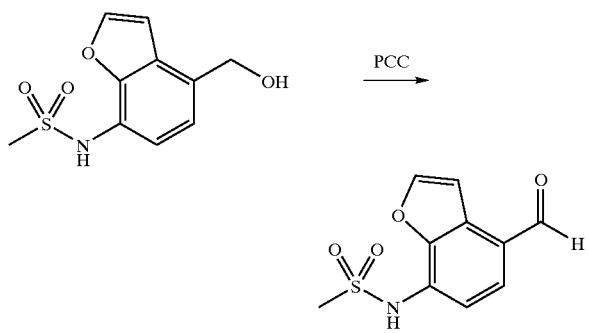

Pyridinium chlorochromate (7.55 g, 35.0 mmole) was added into a solution of N-(4-hydroxymethyl-benzofuran-7-yl)-methanesulfonamide (5.69 g, 23.3 mmole) in dichloromethane (350 mL). The reaction mixture was stirred at room temperature for 16 hr and was partitioned between dichloromethane and water. The organic extract was dried (anhydrous sodium sulfate) and concentrated under reduced pressure. The residue was purified by flash column chromatography over silica gel eluting with 50% ethyl acetate in hexane to give N-(4-formyl-benzofuran-7-yl)-methanesulfonamide as solid (4.8 g, 86%). $^1$H NMR (DMSO-$d_6$) δ: 3.26 (s, 3H), 7.48 (d, 1H, J=8.20 Hz), 7.51 (d, 1H, J=2.10 Hz), 7.88 (d, 1H, J=8.20 Hz), 8.29 (d, 1H, J=2.1 Hz), 10.12 (s, 1H), 10.63 (s, 1H). M−H: 238.

Step 9

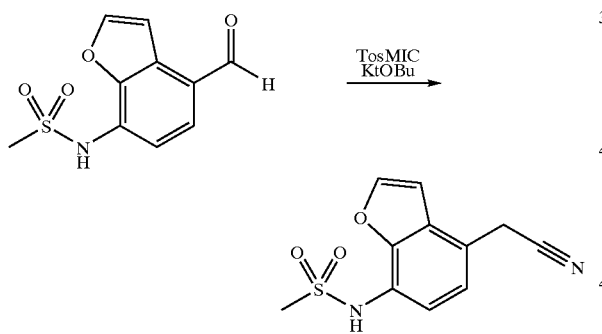

A solution of tosylmethyl isocyanide (1.8 g, 9.22 mmole) in anhydrous ethylene glycol dimethyl ether (60 mL) was added drop-wise into a stirred suspension of potassium tert-butoxide (2.81 g, 25.0 mmole) in anhydrous ethylene glycol dimethyl ether (60 mL) under nitrogen at −65° C. After stirring at −65° C. for 15 min., N-(4-formyl-benzofuran-7-yl)-methanesulfonamide (2.0 g, 8.36 mmole) in anhydrous ethylene glycol dimethyl ether (60 mL) was added drop-wise and the reaction temperature was maintained below −60° C. After stirring for another hour before methanol (30 mL) was added. The reaction mixture was heated to reflux for 20 minutes then stirred at room temperature for 16 hrs. The resulting solution was partitioned between ethyl acetate and aqueous 2% acetic acid. The organic extract was washed with brine, dried (anhydrous sodium sulfate) and concentrated under reduced pressure. The residue was purified by flash column chromatography over silica gel eluting with 40 to and 50% ethyl acetate in hexane to give N-(4-cyanomethyl-benzofuran-7-yl)-methanesulfonamide as a solid (1.31 g, 62%). $^1$H NMR (DMSO-$d_6$) δ: 3.11 (s, 3H), 4.28 (s, 2H), 7.17 (d, 1H, J=2.2 Hz), 7.24–7.30 (m, 2H) 8.15 (d, 1H, J=2.2 Hz), 9.23 (s, 11H) M−H 249.

Step 10

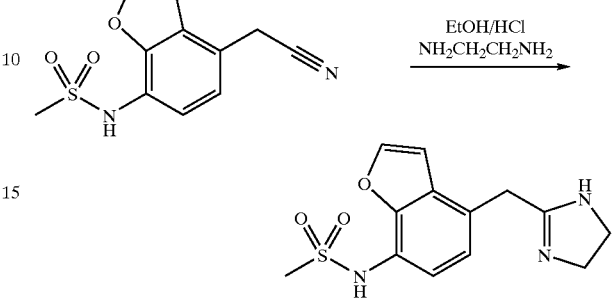

Method A

Hydrogen chloride gas was bubbled to a cold (0° C.) suspension of N-(4-cyanomethyl-benzofuran-7-yl)-methanesulfonamide (0.3 g, 1.2.0 mmole) in anhydrous ethanol (20 mL) for 15 minutes. The reaction mixture was kept in refrigerator for 24 hr. and the solvent removed under reduced pressure. The solid residue was re-dissolved in anhydrous methanol (10 mL) and ethylene diamine (0.085 mL, 1.27 mmoles) was added. The reaction mixture was heated to reflux for 24 hr and the solvent was removed under reduced pressure. The resulting residue was purified by flash column chromatography over silica gel eluting with 8% methanol in dichloromethane with 0.1% concentrated ammonium hydroxide to give N-[4-(4,5-dihydro-1H-imidazol-2-ylmethyl)-benzofuran-7-yl]-methanesulfonamide as a solid (0.28 g, 79%). $^1$H NMR HCl salt (DMSO-$d_6$) δ: 3.11 (s, 3H), 3.83 (s, 4H), 4.16 (s, 2H), 7.24 (m, 2H), 7.38 (d, 1H, J=2.2 Hz), 8.14 (d, 1H, J=2.2 Hz). M+H 294.

Method B

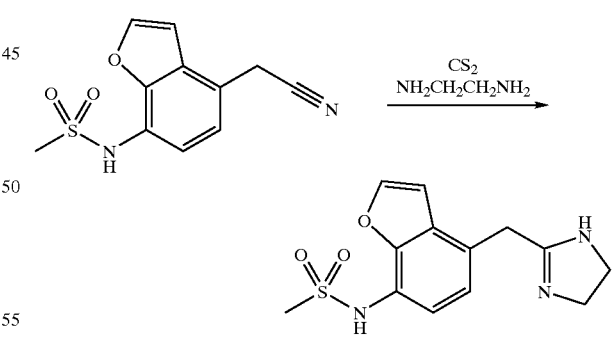

A mixture of N-(4-cyanomethyl-benzofuran-7-yl)-methanesulfonamide (1.0 g, 4.0 mmole), ethylene diamine (8 mL, 119.7 mmoles), and carbon disulfide (one drop) was microwaved at 140° C. for 30 minutes in a Smith creator™. The reaction mixture was transferred into a large beaker (1 L) and the reaction vessel was rinsed with methanol (5 mL). Ether (600 mL) was added to the reaction mixture and insoluble material settled at the bottom of the container. The ether solution was removed by decantation. The residue was purified by flash column chromatography over silica gel eluting with 8% methanol in dichloromethane with 0.1% concentrated ammonium hydroxide to give N-[4-(4,5-dihydro-1H-imidazol-2-ylmethyl)-benzofuran-7-yl]-methanesulfonamide as a solid (1.1 g, 85%).

Step 11

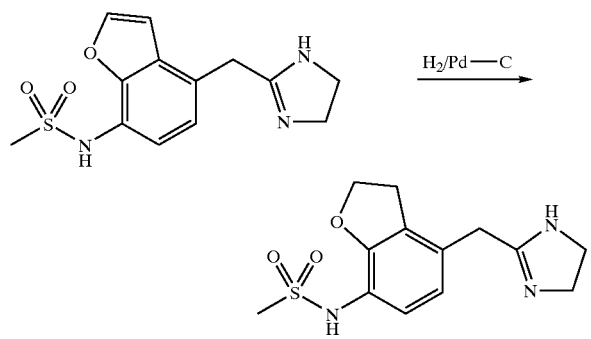

A mixture of N-[4-(4,5-dihydro-1H-imidazol-2-ylmethyl)-benzofuran-7-yl]-methanesulfonamide (44 mg, 0.13 mmoles) and 10% Pd-C (pinch) in methanol (5 mL) was stirred under hydrogen which was supplied by a hydrogen filled balloon, at room temperature for 17 days. The catalyst was removed by filtration through celite. The filtrate was concentrated under reduced pressure. The residue was purified by flash column chromatography over silica gel eluting with 10% to 12% methanol in dichloromethane with 0.1% ammonium hydroxide to give N-[4-(4,5-dihydro-1H-imidazol-2-ylmethyl)-2,3-dihydro-benzofuran-7-yl]-methanesulfonamide as a solid which was further purified by preparative RPHPLC (YMC Combiprep ODS-A column, 10–90% acetonitrile: water (0.1% TFA)) M+H 296. The following representative compounds were synthesized similarly as shown above. Additional compounds prepared according to the procedure of Example 1 are shown in Table 1.

| Structure | Mass Spec. | NMR |
|---|---|---|
| 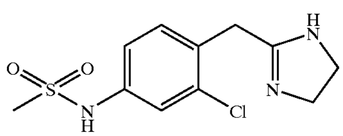 | M + H 288 | $^1$H NMR HCl salt (DMSO-$d_6$) δ: 3.05(s, 3H), 3.82(s, 4H), 3.98(s, 2H), 7.20(dd, 1H, J=8.40, 2.21Hz), 7.32(d, 1H, J=2.21Hz), 7.47(d, 1H, J=8.40z), 10.13(s, 1H), 10.19(s, 1H). |
| 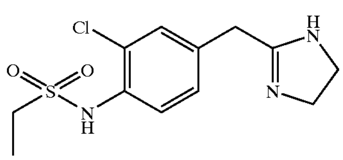 | M + H 302 | $^1$H NMR HCl salt (DMSO-$d_6$) δ: 1.28(t, 3H, J=7.4Hz), 3.14(q, 2H, J=7.4Hz), 3.82(s, 4H), 3.89(s, 2H), 7.38(dd, 1H, J=8.3, 2.0Hz), 7.46(d, 1H, J=8.3Hz), 7.62(d, 1H, J=2.0Hz), 9.51(s, 1H), 10.35(s, 2H). |
| 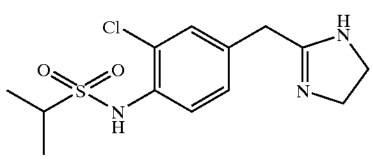 | M + H 316 | $^1$H NMR HCl salt (DMSO-$d_6$) δ: 1.30(d, 6H, J=6.8Hz), 3.27(m, 1H, J=6.8Hz), 3.82(s, 4H), 3.88(s, 2H), 7.36(dd, 1H, J=8.3, 2.0Hz), 7.48(d, 1H, J=8.3Hz), 7.60 (d, 1H, J=2.0Hz), 9.47(s, 1H), 10.32(s, 2H). |

Example 2

This example illustrates a method for producing Compounds of Formula I using the synthetic scheme outlined below:

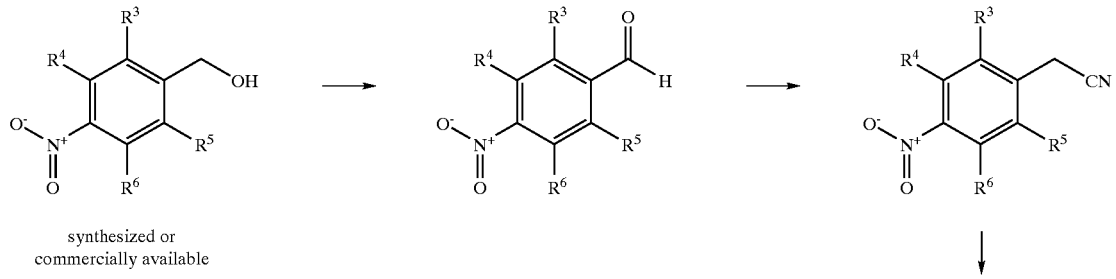

synthesized or
commercially available

Step 1

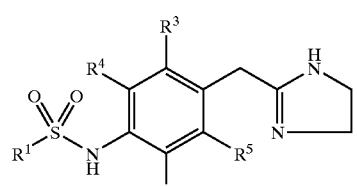 ← 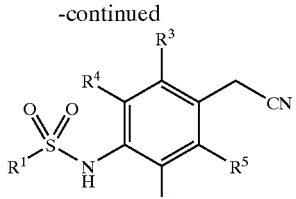 ← 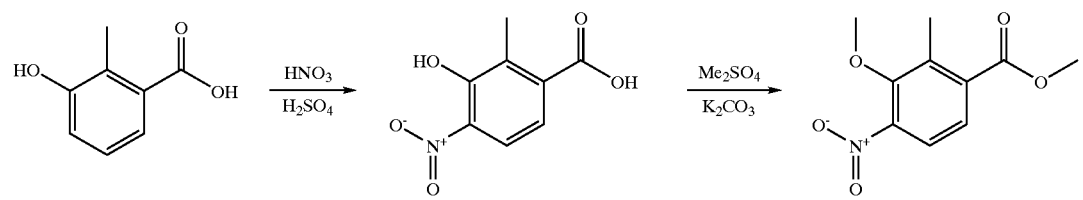

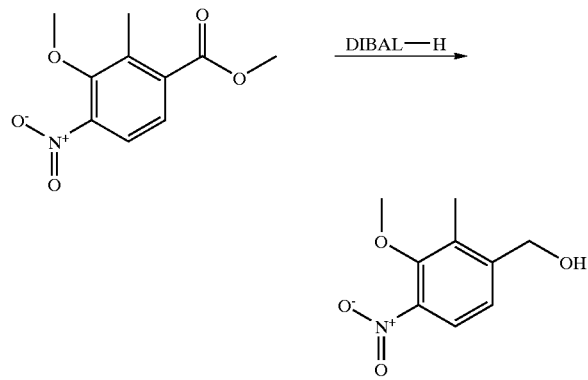

To a stirring mixture of fuming nitric acid (18.7 mL, 0.40 mol) and concentrated sulfuric acid (2.53 mL, 47.5 mmol) at −50° C. was added 3-hydroxy-o-toluic (5.0 g, 32.9 mmol) drop-wise maintaining the reaction temperature at −50° C. After five minutes, the reaction mixture was poured into crushed ice (200 gram) and was extracted with ethyl acetate (400 mL). The ethyl acetate layer was washed with water, dried (anhydrous magnesium sulfate), filtered and concentrated to give a crude product which was a 1:1 mixture of the desired mononitrated product and the undesired bisnitrated product. The crude mixture was re-dissolved in acetone (170 mL). To the resulting solution was added potassium carbonate (20.9 g, 151.0 mmole) and dimethyl sulfate (10.7 mL, 113.2 mmole). The reaction mixture was refluxed for one hour and concentrated. The resulting orange residue was washed with water and air dried and subjected to flash chromatography over silica gel eluting with 10% ethyl acetate/hexane. Product fractions were concentrated under reduced pressure to give 3-methoxy-2-methyl-4-nitrobenzoic acid methyl ester as a solid (1.88 g, 25%). $^1$H NMR (CDCl$_3$) δ: 2.55 (s, 3H), 391 (s,3H), 3.94 (s, 3H, 7.61 (d, 1H, J=8.5 Hz), 7.68 (d, 1H, J=8.6Hz).

Step 2

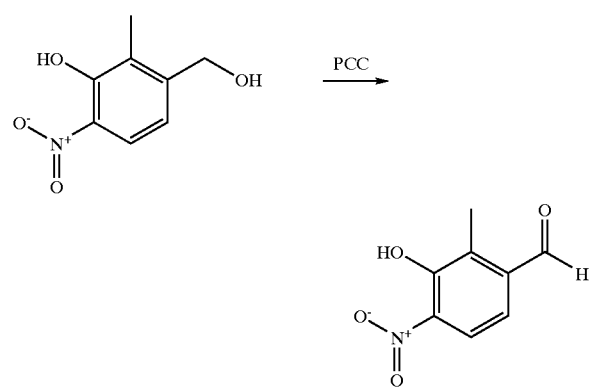

Same procedure as step 7 of Example 1

$^1$H NMR (CDCl$_3$) δ: 1.77 (t, 1H), 2.30 (s, 3H), 3.89 (s, 3H), 4.75 (d, 2H, J=Hz), 7.33 (d, 1H, J=8.3 Hz), 7.70 (d, 1H, J=8.5 Hz).

Step 3

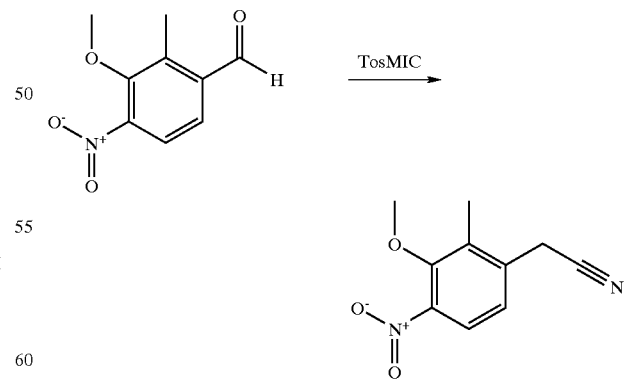

Same procedure as step 8 of Example 1.

$^1$H NMR (CDCl$_3$) δ: 2.67 (s, 3H), 3.93 (s, 3H), 7.70 (s, 2H), 10.34 (s, 1H).

Step 4

Same procedure as step 9 of Example 1.

$^1$H NMR (CDCl$_3$) δ: 2.35 (s, 3H), 3.74 (s, 2H), 3.91 (s, 3H), 7.29 (d, 1H, J=8.4 Hz), 7.70, d, 1H, J=8.4 Hz.

Step 5

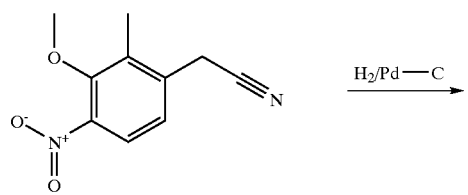

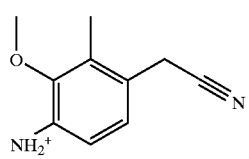

To a solution of (3-methoxy-2-methyl-4-nitro-phenyl)-acetonitnle (1.03 g, 5.0 mmole) in ethanol (100 mL) was added a small amount of 10% palladium on charcoal catalyst and the mixture hydrogenated on the Parr hydrogenator at 45 psi for 3.5 hours. The reaction mixture was filtered through celite and evaporated under reduced pressure to give the (4-amino-3-methoxy-2-methyl-phenyl)acetonitrile as a solid (0.912 g, 100%). $^1$H NMR (CDCl$_3$) δ: 2.25 (s, 3H), 3.56 (s, 2H), 3.72 (s, 3H), 3.85 (br, 2H), 6.60 (d, 1H, J=8.1 Hz), 6.90 (d, 1H, J=8.1 Hz).

Step 6

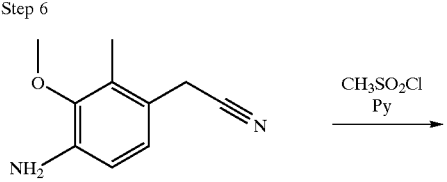

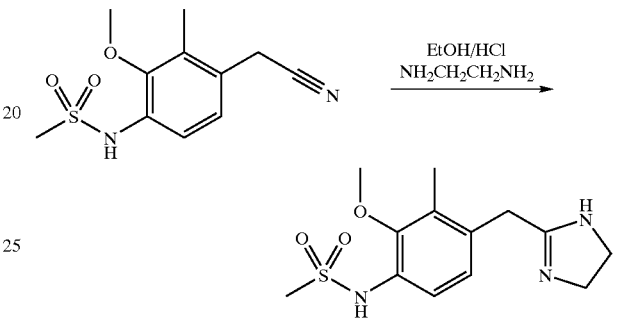

Same procedure as step 6 of Example 1.

$^1$H NMR (CDCl$_3$) δ: 2.31 (s, 3H), 3.06 (s, 3H), 3.64 (s, 2H), 3.76 (s, 3H), 6.98 (br, 1H), 7.13 (d, 1H, J=8.4 Hz), 7.42 (d, 1H, J=8.4 Hz).

Step 7

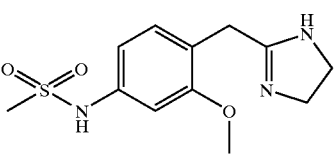

Same procedure as step 10 of Example 1.

$^1$H NMR HCl salt (DMSO-d$_6$) δ: 2.19 (s, 3H), 3.07 (s, 3H), 3.69 (s, 3H), 3.82 (s, 4H), 3.90 (s, 2H), 7.08 (d, 1H, J=8.4 Hz), 7.24 (d, 1H, J=8.4 Hz), 9.11 (s, 1H), 10.24 (s, 2H). M+H 298.

The following representative compounds were synthesized as shown above.

| Structure | Mass Spec. | NMR |
|---|---|---|
| 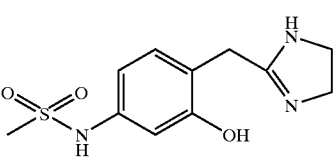 | M + H 284. | $^1$H NMR HCl salt (DMSO-d$_6$) δ: 3.02(s, 3H), 3.75(s, 2H), 3.78(s, 3H), 3.79(s, 4H), 6.82(dd, 1H, J=8.1Hz, 2.0Hz), 6.89(d, 1H, J=2.0Hz), 7.25(d, 1H, J=8.1Hz), 9.92(b, 1H). |
| 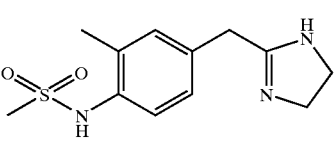 | M + H 270 | $^1$H NMR TFA salt (DMSO-d$_6$), δ: 2.96(s, 3H), 3.76(s, 2H), 3.84(s, 4H), 6.76(dd, 1H, J=1.85, 8.08), 8.78(s, 1H), 10.05(s, 1H), 10.11(s, 1H). |
| 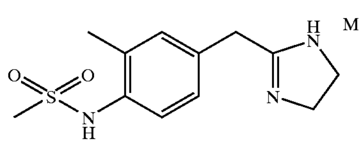 | M + H 288 | $^1$H NMR HCl salt (DMSO-d$_6$) δ: 2.29(s, 3H), 2.98(s, 2H), 3.81(s, 4H), 7.21(m, 3H), 9.13(s, 1H), 10.28(s, 1H). |

| Structure | Mass Spec. | NMR |
|---|---|---|
| 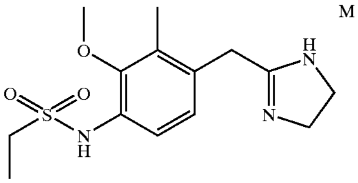 | M + H 312 | ¹H NMR HCl salt (DMSO-$d_6$) δ: 1.26(t, 3H, J=7.3Hz), 2.18(s, 3H), 3.15(q, 2H, J=7.3Hz), 3.17(s, 2H), 3.69(s, 3H), 3.83(s, 4H), 3.86(s, 2H), 7.04(d, 1H, J=8.4Hz), 7.23(d, 1H, J=8.4Hz), 9.09(s, 1H), 10.02(s, 2H). |
| 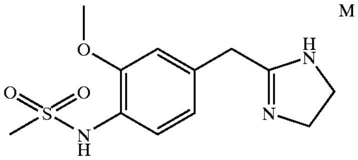 | M + H 284 | ¹H NMR HCl salt (DMSO-$d_6$) δ: 2.95(s, 3H), 3.81(s, 2H), 3.84(s, 4H), 6.92(dd, 1H, J=8.07, 1.79Hz), 7.22(m, 2H), 8.94(s, 1H), 10.32(s, 2H). |
| 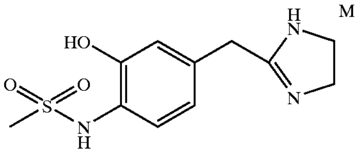 | M + H: 270. | ¹H NMR TFA salt (DMSO-$d_6$) δ: 2.98(s, 3H), 3.69(s, 2H), 3.79(s, 4H), 6.65(dd, 1H, J=8.2Hz, 2.1Hz), 6.83(d, 1H, J=2.1Hz), 7.14(d, 1H, J=8.2Hz), 9.74(s, 1H). |
| 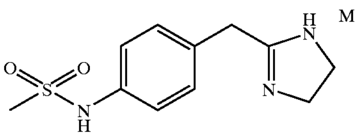 | M + H 254 | ¹H NMR HCl salt (DMSO-$d_6$) δ: 2.99(s, 3H), 3.80(s, 4H), 3.82(s, 2H), 7.19(d, 1H, J=8.34), 7.35(d, 1H, J=8.34), 9.85(s, 1H), 10.28(s, 1H). |

The $2^{nd}$ and the $6^{th}$ compounds in the table above were synthesized by $BBr_3$ cleavage of their corresponding methoxy compounds as follows:

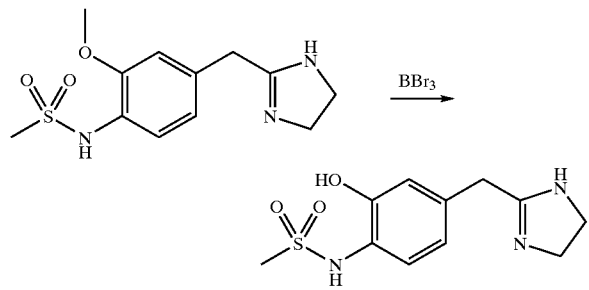

To a suspension of the N-[4-(4,5-dihydro-1H-imidazol-2-ylmethyl)-3-methoxy-phenyl]methanesulfonamide (0.2 gram, 0.71 mmol) in anhydrous dichloromethane (5 mL) at −78° C. was added boron tribromide (1 M solution in methylene chloride, 1.24 g, 4.95 mmol). The reaction mixture was stored in freezer for two days, and then cooled to −78° C. before quenching with methanol (10 mL). The resulting mixture was concentrated under reduced pressure and the residue subjected to reverse phase HPLC purification. RPHPLC (YMC Combiprep ODS-A column, 10–90% acetonitrile: water (0.1% TFA)). The N-[4-(4,5-dihydro-1H-imidazol-2-ylmethyl)-3-hydroxy-phenyl]methanesulfonamide was obtained as trifluoroacetic acid salt (58 mg, 21.5%).

¹H NMR TFA salt (DMSO-$d_6$), δ: 2.96 (s, 3H), 3.76 (s, 2H), 3.84 (s, 4H), 6.76 (dd, 1H, J=1.85, 8.08), 8.78 (s, 1H), 10.05 (s, 1H), 10.11 (s, 1H). M+H 270

Example 3

This example illustrates a method for producing Compounds of Formula I using the synthetic scheme outlined below:

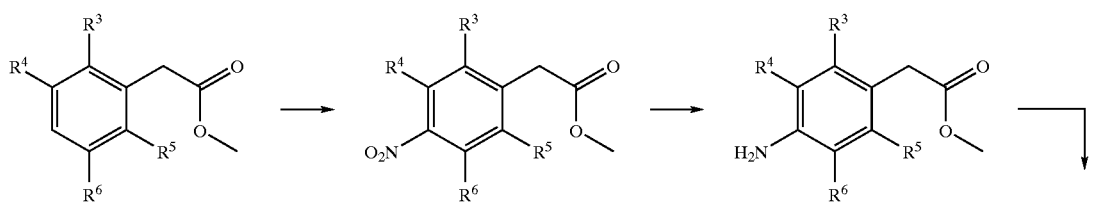

commercially available

Step 1

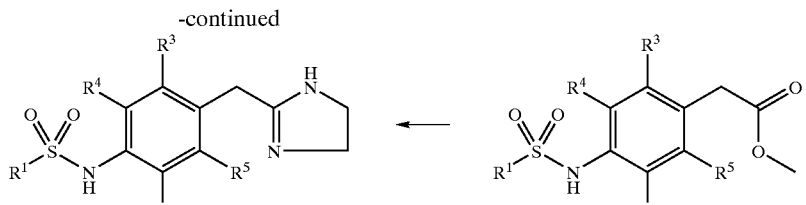

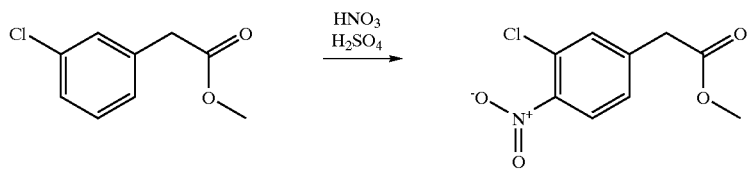

To a solution of (3-chloro-phenyl)acetic acid methyl ester (5.0 g, 27.1 mmol, commercially available) in concentrated sulfuric acid (7.5 mL, 140.7 mmol) at 0° C. was added drop-wise nitric acid (2.52 g, 70%, 28.0 mmol). After stirring at 0° C. for two hrs, the reaction mixture was poured into ice water and was extracted into dichloromethane. The organic extract was washed with brine, dried (anhydrous sodium sulfate), filtered and concentrated under reduced pressure. The residue was purified by flash column chromatography over silica gel eluting with 6% ethyl acetate in hexane to give the desired (3-chloro-4-nitro-phenyl)acetic acid methyl ester as an oil (2.1 g,33%), and (5chloro-2-nitro-phenyl)acetic acid methyl ester as an oil (3.2 g, 51%). $^1$H NMR (CDCl$_3$) δ: 3.69 (s, 2H), 3.74 (s, 3H), 7.33 (dd, 1H, J=8.4 Hz, 1.9 Hz), 7.50 (d, 1H, J=1.8 Hz), 7.87 (d, 1H, J=8.4 Hz.

Step 2

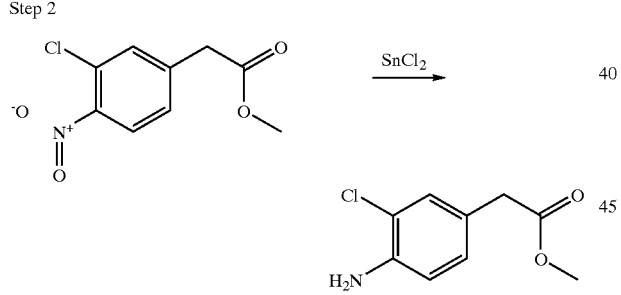

Same procedure as step 5 of Example 1.

$^1$H NMR (CDCl$_3$) δ: 3.49 (s, 2H), 3.69 (s, 3H), 6.72 (d, 1H, J=8.2 Hz), 6.98 (dd, 1H, J=8.2 Hz, 2.0 Hz), 7.18 (d, 1H, J=2.0 Hz).

Step 3

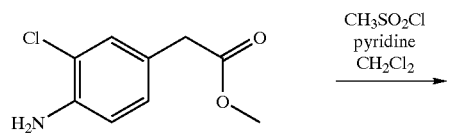

-continued

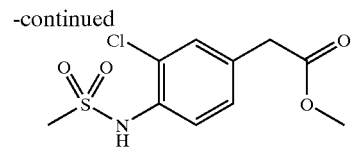

Same procedure as step 6 of Example 1.

$^1$H NMR (CDCl$_3$) δ: 3.01 (s, 3H), 3.60 (s, 2H), 3.72 (s, 3H), 6.78 (b, 1H), 7.22 (dd, 1H, J=8.4 Hz, 1.6 Hz), 7.38 (d, 1H, J=1.6 Hz), 7.61 (d, 1H, J=8.4 Hz).

Step 4

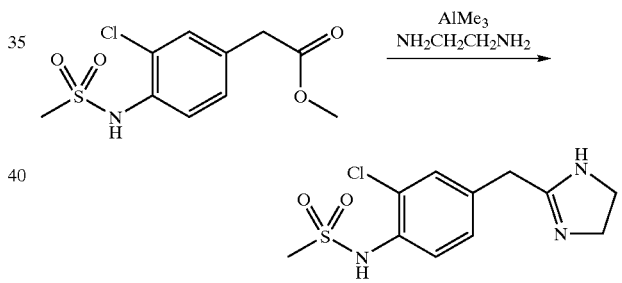

To a solution of trimethylaluminuiim (2.0 M solution in toluene, 7.4 mL, 5.87 mmol) in toluene (30 mL) was added ethylene diamine (0.85 mL, 12.7 mmol) at 0° C. under nitrogen. After stirring at room temperature for one hour, (3-chloro-4-methanesulfonyl-aminophenyl)acetic acid methyl ester (0.7 g, 2.52 mmol) was added and the reaction mixture was heated to reflux for 3 days. The reaction was incomplete and more trimethylaluminum (8 mL, 16 mmol) was added and heating was continued for another day. After solvent was evaporated under reduced pressure, the residue triturated with methyl alcohol and the insoluble material removed by filtration through celite. The filtrate was concentrated under reduced pressure, the residue was purified by flash column chromatography over silica gel eluting with 8% methanol in dichloromethane with 1% ammonium hydroxide to give N-[2-chloro-4-(4,5-dihydro-1H-imidazol-2-ylmethyl)-phenyl]methanesulfonamide as a solid (0.31 g, 43%), which can be re-crystallized from methanol.

$^1$H NMR HCl salt (DMSO-d$_6$) δ: 2.70 (s, 3H), 3.56 (s, 2H), 3.67 (s, 4H), 7.00 (dd, 1H, J=8.4 Hz, 2.2 Hz), 7.23 (d, 1H, J=2.2 Hz), 7.27 (d, 1H, J=8.4 Hz).

Example 4

This example illustrates a method for producing Compounds of Formula I using the synthetic scheme outlined below:

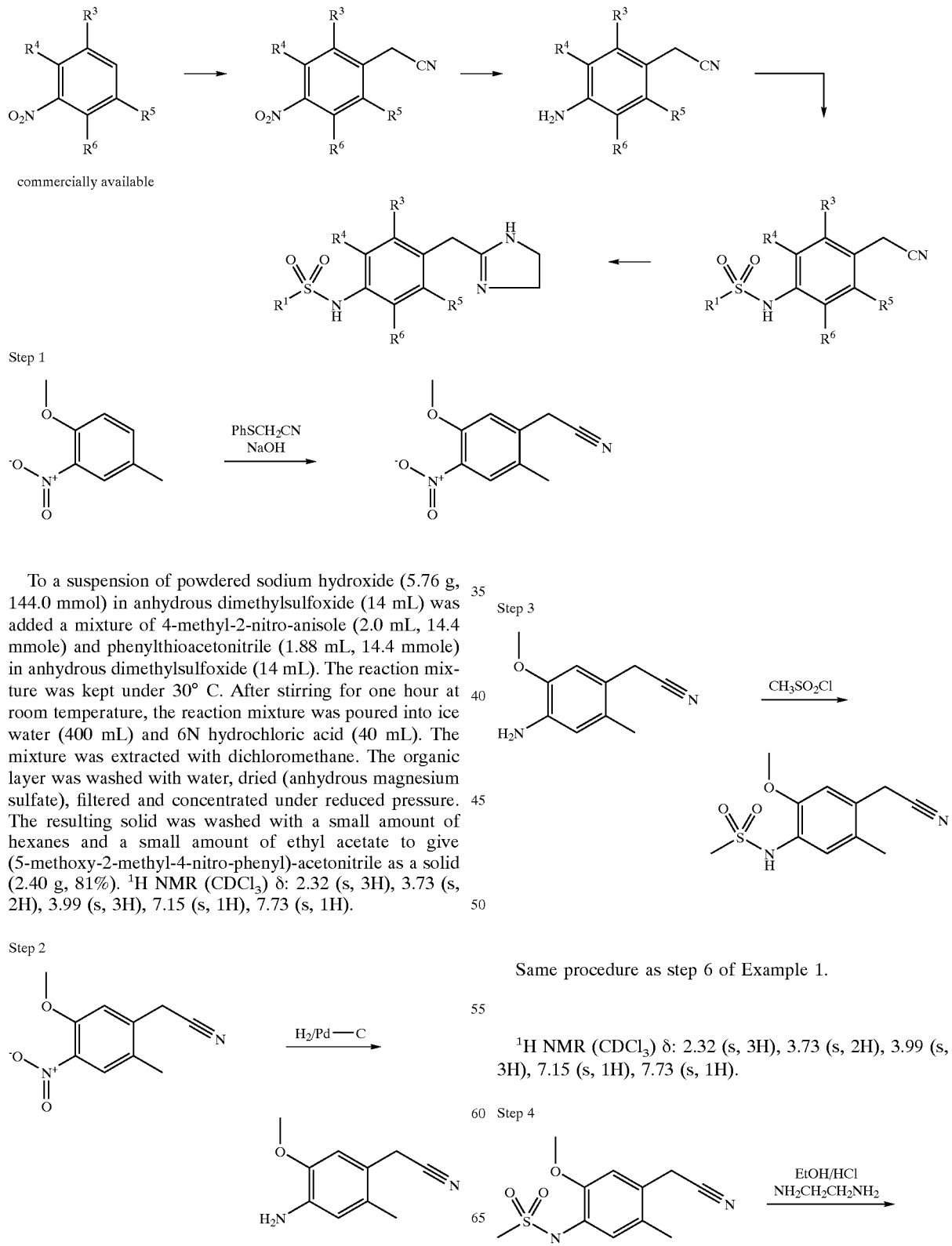

Step 1

To a suspension of powdered sodium hydroxide (5.76 g, 144.0 mmol) in anhydrous dimethylsulfoxide (14 mL) was added a mixture of 4-methyl-2-nitro-anisole (2.0 mL, 14.4 mmole) and phenylthioacetonitrile (1.88 mL, 14.4 mmole) in anhydrous dimethylsulfoxide (14 mL). The reaction mixture was kept under 30° C. After stirring for one hour at room temperature, the reaction mixture was poured into ice water (400 mL) and 6N hydrochloric acid (40 mL). The mixture was extracted with dichloromethane. The organic layer was washed with water, dried (anhydrous magnesium sulfate), filtered and concentrated under reduced pressure. The resulting solid was washed with a small amount of hexanes and a small amount of ethyl acetate to give (5-methoxy-2-methyl-4-nitro-phenyl)-acetonitrile as a solid (2.40 g, 81%). $^1$H NMR (CDCl$_3$) δ: 2.32 (s, 3H), 3.73 (s, 2H), 3.99 (s, 3H), 7.15 (s, 1H), 7.73 (s, 1H).

Step 2

Same procedure as step 5 of Example 2.

$^1$H NMR (CDCl$_3$) δ: 2.19 (s, 3H), 3.57 (s, 2H), 3.78 (br, 2H), 3.85, s, 3H), 6.55 (s, 1H), 6.74 (s, 1H).

Step 3

Same procedure as step 6 of Example 1.

$^1$H NMR (CDCl$_3$) δ: 2.32 (s, 3H), 3.73 (s, 2H), 3.99 (s, 3H), 7.15 (s, 1H), 7.73 (s, 1H).

Step 4

-continued

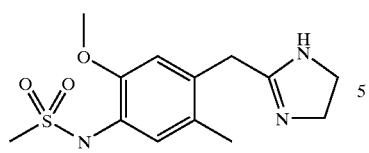

Same procedure as step 10 of Example 1.

$^1$H NMR HCl salt (DMSO-d$^6$) δ: 2.20 (s, 3H), 2.95 (s, 3H), 3.82 (s, 3H), 3.83 (s, 4H), 3.87 (s, 2H), 7.10 (s, 1H), 7.13 (s, 1H), 8.88 (s, 1H), 10.19 (s, 2H). M+H 298.

The following representative compounds were also synthesized using procedures of Example 4 above. Additional compounds prepared according to the procedure of Example 4 are shown in Table 1.

| Structure | Mass Spec. | NMR |
|---|---|---|
| | M + H 302 | $^1$H NHM HCl salt (DMSO-d$_6$) δ: 2.26(s, 3H), 2.79(s, 3H), 3.56(s, 4H), 3.60(s, 2H), 7.03(d, 1H, J=8.3Hz), 7.18(d, 1H, J=8.3Hz). |
| | M + H 302 | $^1$H NMR HCl salt (DMSO-d$_6$) δ: 3.02(s, 3H), 3.82(s, 3H), 3.84(s, 4H), 7.13(d, 1H J=10.75Hz), 7.31(d, 1H, J=6.99Hz), 9.19(s, 1H), 10.38(s, 2H). |
| 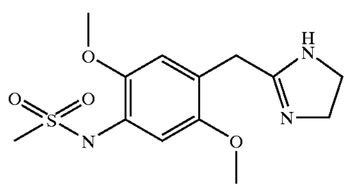 | M + H 314 | $^1$H NMR HCl salt (DMSO-d$_6$) δ: 2.98(s, 3H), 3.75(s, 3H), 3.80(s, 6H), 6.95(s, 1H), 7.18(s, 1H), 8.99(s, 1H), 10.01(s, 2H). |
| 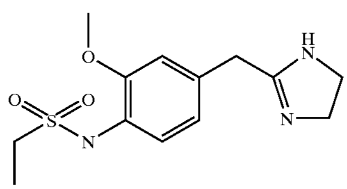 | M + H 298 | $^1$H NMR (DMSO-d$_6$) δ: 1.24(t, 3H, J=7.3Hz), 3.02(q, 2H, J=7.3Hz), 3.81(s, 4H), 3.84(s, 5H), 6.94(dd, 1H, J=8.1, 1.71Hz), 7.24(d, 1H, J=8.1Hz), 7.25(d, 1H, J=1.7Hz), 8.92(s, 1H), 10.41(s, 2H). |
| 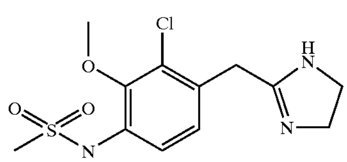 | M + H 318. | $^1$H NMR HCl salt (DMSO-d$_6$) δ: 2.88(s, 3H), 3.55(s, 4H), 3.62(s, 2H), 3.75(s, 3H), 7.00(d, 1H, J=8.5Hz), 7.25(d, 1H, J=8.5Hz). |
| | M + H 302 | $^1$H NMR HCl Salt (DMSO-d$_6$) δ: 2.26(s, 3H), 3.05(s, 3H), 3.83(s, 4H), 3.91(s, 2H), 7.31(s, 1H), 7.51(s, 1H), 9.47(s, 1H), 10.15(s, 2H). |
| 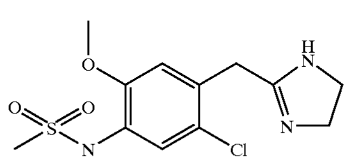 | M + H 318 | $^1$H NMR HCl salt (DMSO-d$_6$) δ: 3.02(s, 3H), 3.83(s, 4H), 3.87(s, 3H), 4.00(s, 2H), 7.34(s, 1H), 7.37(s, 1H), 9.23(s, 1H), 10.20(s, 2H). |

| Structure | Mass Spec. | NMR |
|---|---|---|
| [structure] | M + H 298 | $^1$H NMR HCl salt (DMSO-$d_6$) δ: 2.28 (s, 3H), 2.96(s, 3H), 3.79(s, 2H), 3.83(s, 4H), 6.88(s, 1H), 7.10(s, 1H), 8.71(s, 1H), 10.40(s, 2H). |
| [structure] | M + H 298 | $^1$H NMR HCl salt (DMSO-$d_6$) δ: 1.38(t, 3H, J=7.12Hz), 2.95(s, 3H), 3.81(s, 4H), 3.83(s, 2H), 4.09(q, 2H, J=7.12Hz), 6.91(dd, 1H, J=8.22 1.81Hz), 7.19(m, 1H). |
| [structure] | M + H 332 | $^1$H-NMR HCl Salt (DMSO-$d_6$) δ: 3.07(s, 3H), 3.82(s, 4H), 3.90(s, 2H), 7.44(d, 2H), 7.79(s, 1H), 9.45(s, 1H), 10.34(s, 2H). |
| [structure] | M + H 360 | $^1$H-NMR HCl salt (DMSO-$d_6$) δ: 1.20(t, 3H, J=7.30Hz), 2.31(s, 3H), 2.88(q, 2H, J=7.3Hz), 3.58(s, 4H), 3.62(s, 2H), 7.03(d, 1H, J=8.30Hz), 7.18(d, 1H, J=8.30Hz). |
| [structure] | M + H 316 | $^1$H-NMR HCl salt (DMSO-$d_6$) δ: 1.27(t, 3H, J=7.30Hz), 2.33(s, 3H), 3.13(q, 2H, J=7.3Hz), 3.82(s, 4H), 4.01(s, 2H), 7.33(s, 2H,), 9.44(s, 1H), 10.27( s, 2H). |

Example 5

This example illustrates a various formulations of Compounds of Formula I.

I. Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

II. Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

III. Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |

-continued

III. Composition for Oral Administration

| Ingredient | Amount |
| --- | --- |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

IV. Parenteral Formulation

| Ingredient | % wt./wt. |
| --- | --- |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

V. Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

VI. Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

VII. Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH.

The nasal spray formulations may be delivered via a nasal spray metered pump typically delivering about 50–100 microliters of formulation per actuation. A typical dosing schedule is 2–4 sprays every 4–12 hours.

Example 6

This example illustrates a functional assay which can be used to determine $\alpha_{1A/L}$ agonist activity of Compounds of Formula I.

The activity of compounds of this invention in vitro was examined using fluorescent dye determination of intracellular calcium concentrations.

Fluo-3 loaded cell preparation:

Chinese hamster ovary cells CHO-K1 expressing the alpha 1A adrenoceptors (clone 13) are washed 4 times (approx. 300 $\mu$L/well) with fluorometric imaging plate reader (FLIPR) buffer (Hank's buffered saline solution (HBSS), 2 mM $CaCl_2$, 10 mM HEPES, 2,5 mM probenecid, 100 $\mu$M ascorbic acid), with a final volume of 150 $\mu$L/well. Cells are loaded with 50 $\mu$L/well of 8 $\mu$M Fluo-3 AM (Molecular Probes, Eugene, OR), for a final concentration of 2 $\mu$M Fluo-3 AM. Cells are then incubated for 60 min at 37° C. Following dye loading, cells are washed 4 times (approx. 300 $\mu$L/well) with FLIPR buffer with a final volume of 150 $\mu$L/well.

Agonist Assay

Test compound, control compound and reference compound are run in quadruplicate, 8-point curves on each plate with a final assay concentration range of $10^{-4}$ M to $10^{-11}$ M for each compound. All compounds are dissolved in DMSO at 10 mM, and serially diluted in FLIPR buffer.

The assay plate is placed in the FLIPR incubation chamber and a baseline fluorescence measurement (excitation @ 488 nm and emission @ 510–570 nm) is obtained (15 sec interval). An experimental run is then commenced. The reaction is started with the addition of 50 $\mu$L/well (at 4×final concentration) of test, control, or reference compound solution from the agonist plate to the assay plate to all 96 wells simultaneously. Fluorescence is measured for 120 sec at 1 sec intervals. Then, a second addition of 5 $\mu$M ionomycin (50 $\mu$L/well from 5×concentration ionomycin plate) is added to the assay plate. Fluorescence is measured for 30 sec at 1 sec intervals. All experiments are conducted at room temperature.

Measurements

For each assay plate, responses (increase in peak fluorescence) in each well following addition of agonist (test, control and reference) are determined. These responses may be expressed as raw CFU (Corrected Fluorescence Units), as a % maximum ionomycin response or other unit as determined by the investigator.

Statistics

For test compound, control compound (Norepinephrine (NE) bitartrate), and reference compound, the concentration producing a 50% increase in control response ($EC_{50}$) is determined using iterative curve-fitting methods. Excel spreadsheet or Kaleidagraph software are used to fit data to the general logistic function ($E = B + E_{max} \cdot A^{nH}/A^{nH} + EC_{50}^{nH}$), where B is the corrected baseline fluorescence units (defined as zero), A is the concentration of agonist added and nH is the Hill slope (constrained to unity). $EC_{50}$ values and maxima ($E_{max}$) for each curve can be estimated objectively using this software.

In addition, the intrinsic activity ($\alpha$) is determined. Intrinsic activity is defined as the maximum response to test agonist divided by the maximum response to a full agonist acting through the same receptor. For these experiments, the full agonist is defined as Norepinephrine (NE) bitartrate (control).

As used herein an agonist is a compound that elicits a maximal response greater than 50% of that of norepinephrine with a $pEC_{50} > 5.5$.

Data for representative compounds of the invention are shown below.

extraneous tissue was dissected away, and tissues were placed in oxygenated Krebs' solution (mM; NaCl, 118.5; $NaHCO_3$, 25; dextrose, 5: KCl, 4.8; $CaCl_2$, 2.5; $MgSO_4$, 1.2 and $KH_2PO_4$, 1.2). Cocaine (30 $\mu$M), corticosterone (30 $\mu$M), ascorbic acid (100 $\mu$M), indomethacin (10 $\mu$M) and propranolol (1 $\mu$M) were added to the Krebs' solution to block neuronal uptake, extraneuronal uptake, auto-oxidation of catecholamines, prostanoid synthesis, beta-adrenoceptors, respectively. The $\alpha_2$-adrenoceptor antagonist

| Cpd. No. | Structure | CHO-1A-13 pEC50 | CHO-1A-13 IA |
| --- | --- | --- | --- |
| 2 | 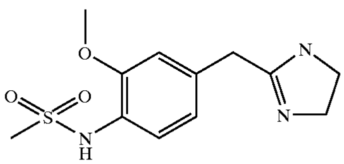 | 6.77 | 0.92 |
| 6 | 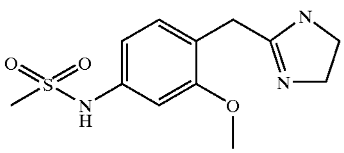 | 6.46 | 0.43 |
| 8 | 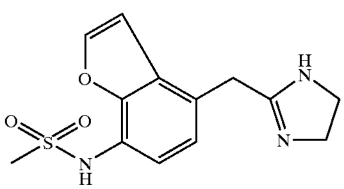 | 6.52 | 0.65 |
| 13 | 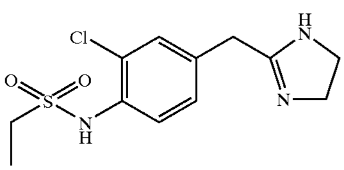 | 6.18 | 0.16 |
| 25 | 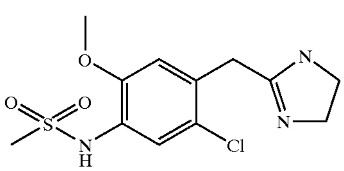 | 7.12 | 0.81 |
| 22 | 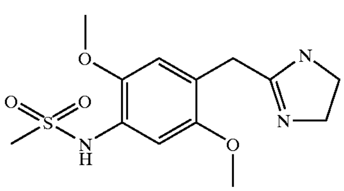 | 6.16 | 0.27 |

Example 7

This example illustrates an assay for determining $\alpha_{1A/L}$-adrenoceptor activity of compounds of Formula I.

Compounds used in this example were from Sigma Chemical Co., St. Louis, Mo., U.S.A.) unless specified otherwise.

In vitro

Male white New Zealand rabbits (3–3.5 kg) and Sprague-Dawley rats (250–400 g) were euthanized by $CO_2$ asphyxiation. The bladder (rabbit) or aorta (rat) were removed, idazoxan (0.3 $\mu$M, Research Biochemicals, Inc., Natick, Mass., U.S.A.) and the calcium channel antagonist nitrendipine (1 $\mu$M, Research Biochemico International, Natick, Mass., U.S.A.) were added the Krebs' solution for rabbit and rat experiments, respectively. Strips of bladder neck (rabbit) approximately 0.8–1.2 cm in length and 2–3 mm in width and aortic rings (2–4 per rat) approximately 3 mm in width, cut as near the heart as possible, were suspended in water-jacketed tissue baths at a resting tension of 1. Tissues were maintained at 34° C. and bubbled continuously with an oxygen/carbon dioxide mixture.

Tissues were primed with norepinephrine (10 μM) and washed for 60 minutes before constructing a first cumulative concentration-effect to norepinephrine. Tissues were then washed for 60 minutes before constructing a second concentration-effect curve to a test agonist. The concentration producing the half maximal response ($pEC_{50}$) and the intrinsic activity (relative to norepinephrine) were recorded. Results for standards and representative compounds of the present invention were determined. Representative compounds of the invention showed activity in this assay.

Example 8

This example illustrates IUP and MAP Experimental Protocol.

In preparation for surgery, Dutch Belted rabbits were anesthetized, shaved and administered hydration fluids. The femoral vein and artery were then isolated and cannulated for the administration of test compounds and the measurement of blood pressure, respectively. Following laparotomy, the ureters were isolated, cannulated and exteriorized. The urethra was isolated and catheterized with a balloon tipped urethral catheter (PE-100 tubing), with the balloon being placed at a level just proximal to the pubic bone.

Following a recovery period, animals were instrumented with Gould pressure transducers (P23XL) connected to an ADInstruments PowerLab data acquisition system. After a 60-minute stabilization period, the positive control amidephrine (316 μg/kg, 1 ml/kg, in saline,) was administered intravenously (i.v.). One hundred and twenty minutes later, Compounds of Formula I (0.001–3 mg/kg, 1 ml/kg, in 5% DMSO, i.v.) were administered. Doses were given at 15-minute intervals or after baseline were re-established. At the end of the experiment, the rabbits were euthanized by an overdose of pentobarbital sodium (i.v.). All procedures were carried out after approval by the Roche Bioscience Institutional animal Care and use Committee.

Baseline intraurethral pressure (IUP) and mean arterial pressure (MAP) were calculated as the mean of the time period occurring 30 seconds before each dose of vehicle or test compound was administered. Compound effect was calculated as the mean of the time period occurring 20 seconds after vehicle or test compound was administered (post dose value). IUP and MAP changes induced by the test compounds were calculated by subtracting their respective baseline values from the post-dose values.

For statistical analysis, the treatment groups were compared with respect to IUP or MAP, by analysis of variance. Pairwise comparisons of the treatment groups to the vehicle groups were made using Fisher's LSD test with Bonferroni's adjustment, if the overall difference was not significant. To estimate the $ED_{50}$, the % positive control was first calculated for each animal, then the $ED_{50}$ for the test compound was estimated by fitting a sigmoidal model to the % positive control data.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

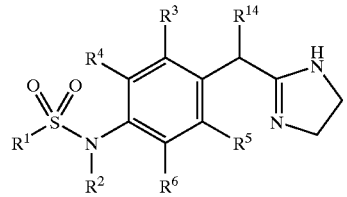

a pharmaceutically acceptable salt or a prodrug thereof, wherein
$R^1$ is alkyl or —$NR^7R^8$, where each of $R^7$ and $R^8$ is independently hydrogen or alkyl;
$R^2$ is hydrogen or alkyl;
each of $R^3$, $R^4$, $R^5$; and $R^6$ is independently hydrogen, halide, alkyl, —$OR^9$ (where $R^9$ is hydrogen, alkyl, a hydroxy protecting group, or cycloalkylalkyl), —$SR^{10}$ (where $R^{10}$ is hydrogen or alkyl), or —$NR^{11}R^{12}$ (where each of $R^{11}$ and $R^{12}$ is independently hydrogen, alkyl, or a nitrogen protecting group), provided $R^3$, $R^4$, $R^5$, and $R^6$ are not all simultaneously alkyl); or $R^3$ and $R^4$ together with atoms to which they are attached to form heterocyclyl, heteroaryl, or cycloalkyl; and
$R^{14}$ is hydrogen, lower alkyl or —$OR^{15}$, where $R^{15}$ is hydrogen, lower alkyl, or a hydroxy protecting group.

2. The compound according to claim 1, wherein $R^{14}$ is hydrogen.

3. The compound according to claim 2, wherein $R^1$ is alkyl.

4. The compound according to claim 3, wherein $R^1$ is selected from the group consisting of methyl, ethyl, and isopropyl.

5. The compound according to claim 3, wherein $R^2$ is hydrogen.

6. The compound according to claim 5, wherein each of $R^7$ and $R^8$ is independently hydrogen or methyl.

7. The compound according to claim 6, wherein each of $R^3$, $R^4$, $R^5$, and $R^6$ is independently hydrogen, halide, alkyl, or —$OR^9$, where $R^9$ is hydrogen, alkyl, a hydroxy protecting group, or cycloalkylalkyl; or $R^3$ and $R^4$ together with atoms to which they are attached to form heterocyclyl, heteroaryl, or cycloalkyl.

8. The compound according to claim 7, wherein at least one of $R^3$, $R^4$, $R^5$, and $R^6$ alkyl, halide, or —$OR^9$.

9. The compound according to claim 8, wherein at least one of $R^3$, $R^4$, $R^5$, and $R^6$ is bromo, chloro, fluoro, methoxy, ethoxy, methyl, and hydroxy.

10. The compound according to claim 9, wherein
(a) $R^3$ is methoxy, and $R^4$, $R^5$, and $R^6$ are hydrogen;
(b) $R^3$ is methyl, $R^6$ is methoxy, and $R^4$ and $R^5$ are hydrogen;
(c) $R^3$ is methyl, $R^6$ is chloro, and $R^4$ and $R^5$ are hydrogen;
(d) $R^3$ is chloro, $R^4$ is methoxy, and $R^5$ and $R^6$ are hydrogen;
(e) $R^3$ is methyl, $R^4$ is chloro, and $R^5$ and $R^6$ are hydrogen;
(f) $R^3$ is methyl, $R^4$ is methoxy, and $R^5$ and $R^6$ are hydrogen;
(g) $R^4$ is chloro, and $R^3$, $R^5$ and $R^6$ are hydrogen;
(h) $R^4$ is methoxy, and $R^3$, $R^5$, and $R^6$ are hydrogen;
(i) $R^3$ is methyl, $R^6$ is bromo, and $R^4$ and $R^5$ are hydrogen;

(j) $R^3$ is bromo, $R^4$ is methoxy, and $R^5$ and $R^6$ are hydrogen;

(k) $R^3$ is methyl, $R^4$ is bromo, and $R^5$ and $R^6$ are hydrogen;

(l) $R^4$ is bromo, and $R^3$, $R^5$ and $R^6$ are hydrogen; and (m) $R^3$ is ethoxy and $R^4$, $R^5$ and $R^6$ are hydrogen.

11. The compound according to claim 7, wherein $R^3$ and $R^4$ together with atoms to which they are attached to form furanyl, dihydrofuranyl, or pyrrolyl.

12. The compound according to claim 11, wherein $R^3$ and $R^4$ together with atoms to which they are attached to form furanyl or dihydrofuranyl.

13. The compound according to claim 12, wherein said compound is of the formula:

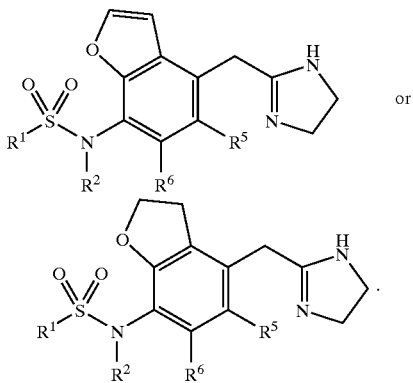

or

14. A method for producing an imidazolin-2-ylmethyl-substituted aromatic compound of the formula:

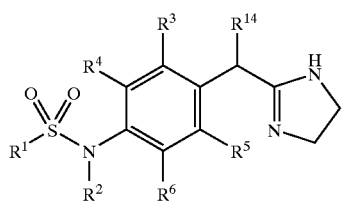

said method comprising contacting a nitrile compound of the formula:

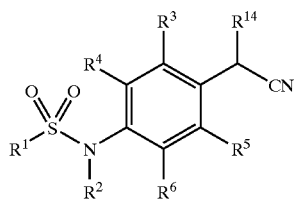

with ethylene diamine to produce the imidazolin-2-ylmethylsubstituted aromatic compound, wherein $R^1$ is alkyl, —$NR^7R^8$, where each of $R^7$ and $R^8$ is independently hydrogen or alkyl;

$R^2$ is hydrogen or alkyl;

each of $R^3$, $R^4$, $R^5$, and $R^6$ is independently hydrogen, halide, alkyl, —$OR^9$, where $R^9$ is hydrogen, alkyl, a hydroxy protecting group, or cycloalkylalkyl, —$SR^{10}$, where $R^{10}$ is hydrogen or alkyl, or —$NR^{11}R^{12}$, where each of $R^{11}$ and $R^{12}$ is independently hydrogen, alkyl, or a nitrogen protecting group, provided $R^3$, $R^4$, $R^5$, and $R^6$ are not all simultaneously alkyl); or $R^3$ and $R^4$ together with atoms to which they are attached to form heterocyclyl, heteroaryl, or cycloalkyl; and $R^{14}$ is hydrogen, lower alkyl or —$OR^{15}$, where $R^{15}$ is hydrogen, lower alkyl, or a hydroxy protecting group.

15. A method for producing an imidazolin-2-ylmethyl-substituted aromatic compound of the formula:

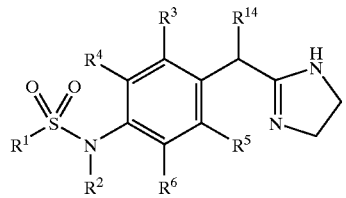

said method comprising contacting an ester compound of the formula:

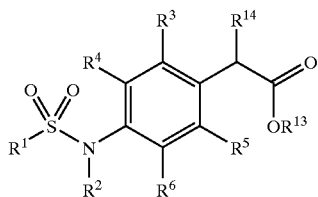

with ethylene diamine in the presence of a trialkylaluminum to produce the imidazolin-2-ylmethyl-substituted aromatic compound, wherein $R^1$ is alkyl, —$NR^7R^8$, where each of $R^7$ and $R^8$ is independently hydrogen or alkyl;

$R^2$ is hydrogen or alkyl;

each of $R^3$, $R^4$, $R^5$, and $R^6$ is independently hydrogen, halide, alkyl, —$OR^9$, where $R^9$ is hydrogen, alkyl, a hydroxy protecting group, or cycloalkylalkyl, —$SR^{10}$, where $R^{10}$ is hydrogen or alkyl, or —$NR^{11}R^{12}$, where each of $R^{11}$ and $R^{12}$ is independently hydrogen, alkyl, or a nitrogen protecting group; or $R^3$ and $R^4$ together with atoms to which they are attached to form heterocyclyl, heteroaryl, or cycloalkyl;

$R^{13}$ is alkyl; and $R^{14}$ is hydrogen, lower alkyl or —$OR^{15}$, where $R^{15}$ is hydrogen, lower alkyl, or a hydroxy protecting group.

16. The method of claim 15, wherein the trialkylaluminum is trimethylaluuminum or triethylaluminum.

17. A composition comprising:

(a) a therapeutically effective amount of a compound of claim 1; and (b) a pharmaceutically acceptable carrier.

18. A method for treating a disease state selected from the groups consisting of urge incontinence, stress incontinence, overflow incontinence, functional incontinence, sexual dysfunction, nasal congestion, and CNS disorders selected from the group depression, anxiety, dementia, senility, Alzheimer's, deficiencies in attentiveness and cognition, eating disorders, obesity, bulimia and anorexia, said method comprising administering to a patient in need of such treatment a therarpeutically effective amount of a compound of claim 1.

19. A method for treating a disease stat comprising urinary incontinence by administering to a subject in need of such treatment an effective amount of a Compound of claim 1.

20. The method of claim 19, wherein the disorder is stress incontinence.

21. The method of claim 19, wherein the disorder is urge incontinence.

22. A method for treating nasal congestion by administering to a mammal in need of such treatment an effective amount of a Compound of claim 1.

23. The method of claim 22, wherein the nasal congestion is sinusitis or otitis.

24. The method of claim 23, wherein the disorder is sinusitis or otitis.

25. A method for treating sexual dysfunction by administering to a mammal in need of such treatment an effective amount of a Compound of claim 1.

26. The compound of claim 1, wherein $R^1$ is methyl or ethyl.

27. The compound of claim 26, wherein $R^4$ and $R^5$ each independently is: hyrdogen; methyl; fluoro; chloro; methoxy; ethoxy; or cyclopropylmethoxy.

28. The compound of claim 26, wherein $R^5$ is hydrogen and $R^4$ is: halo; alkyl; alkoxy; hydroxy; or cycloalkylalkyloxy.

29. The compound of claim 26, wherein $R^5$ is $R^4$ is: methyl; fluoro; chloro; methoxy; ethoxy; or cyclopropylmethoxy.

30. The compound of claim 26, wherein $R^5$ is hydrogen and $R^4$ is halo or alkoxy.

31. The compound of claim 26, wherein $R^5$ is hydrogen and $R^4$ is fluoro, chloro, methoxy or ethoxy.

32. The compound of claim 31, wherein $R^4$ is chloro.

33. The compound of claim 26, wherein $R^4$ is hydrogen and $R^5$ is: halo; alkyl; alkoxy; hydroxy; or cycloalkylalkyloxy.

34. The compound of claim 26, wherein $R^4$ is hydrogen and $R^5$ is: methyl; fluoro; chloro; methoxy; ethoxy; or cyclopropylmethoxy.

35. The compound of claim 26, wherein $R^4$ is hydrogen and $R^5$ is halo or alkoxy.

36. The compound of claim 26, wherein $R^4$ is hydrogen and $R^5$ is fluoro, chloro, methoxy or ethoxy.

37. The compound of claim 26, wherein $R^4$ is hydrogen and $R^5$ is ethoxy.

38. The compound of claim 25, wherein said compound is selected from:

N-[4-(4,5-Dihydro-1H-imidazol-2-ylmethyl)-phenyl]-methanesulfonamide;

N-[4-(4,5-Dihydro-1H-imidazol-2-ylmethyl)-2-methoxy-phenyl]-methanesulfonamide;

N-[4-(4,5-Dihydro-1H-imidazol-2-ylmethyl)-2-methyl-phenyl]-methanesulfonamide;

N-[2- Chloro-4-(4,5-dihydro-1H-imizazol-2-ylmethyl)-phenyl]- methanesulfonamide;

N-[4-(4,5-Dihydro-1H-imidazol-2-ylmethyl)-2-hydroxy-phenyl]-methanesulfonamide;

N-{4-[(4,5-Dihydro-]H-imidazol-2-yl)-hydroxy-methyl]-2-methoxy-phenyl}- methanesulfonamide;

Ethanesulfonic acid [2-chloro-4-(4,5-dihydro-)H-imidazol-2ylmethyl)-phenyl]-amide;

Propane-2-sulfonic acid [2-chloro-4(4,5- dihydro-1H-imidazol-2-ylmethyl)-phenyl]-amide;

N-[4-(4,5-Dihydro-1H-imidazol-2-ylmethyl)-5fluoro-2-methoxy-phenyl]-methanesulfonamide;[[;]]

N-[4-(4,5-Dihydro-1H-imidazol-2-ylmethyl)-2-methoxy-5-methyl-phenyl]-methanesulfonamide;

N-[2-Chloro-4-(4,5-dihydro-1H-imidazol-2-ylmethyl)-5-methoxy-phenyl]-methanesulfonamide;

N-[4-(4,5-Dihydro-1H-imidazol-2-ylmethyl)-2,5-dimethoxy-phenyl]-methanesulfonamide;

N-[4-(4,5-Dihydro-1H-imidazol-2-ylmethyl)2-methoxy-5methyl-phenyl]-methanesulfonamide;

N-[5-Chloro-4-(4,5-dihydro-1H-imidazol-2-methyl)-2-methoxy-phenyl]-methanesulfonamide;

N-[2-Chloro-4-(4,5-dihydro-1H-imidazol-2-ylmethyl)-5-methyl-phenyl]-methanesulfonamide;

N-[2-Ethoxy-4-(4,5-dihydro-1H-imidazol-2-ylmethyl)-phenyl]-methanesulfonamide;

Ethanesulfonic acid [4-(4,5-dihydro-1H-imidazol-2ylmethyl)-2-methoxy-phenyl]-amide;

N-[2-Bromo-4-(4,5-dihydro-1H-imidazol-2ylmethyl)-phenyl]-methanesulfonamide;

N-[2-Chloro-4-(4,5-dihydro-1H-imidazol-2-ylmethyl)-5fluoro-phenyl]-methanesulfonamide;

N-[4-(4,5-Dihydro-1H-imidazol-2-ylmethyl)-2-hydroxy-5-methoxy-phenyl]-methanesulfonamide; and N-[4-(4,5-Dihydro-1H-imidazol-2-ylmethyl)-2-fluoro-phenyl]-methanesulfonamide.

39. A composition comprising:

(a) a therapeutically effective amount of a compound of claim 25 and (b) a pharmaceutically acceptable carrier.

40. A method for treating a disease state selected from the groups consisting of urge incontinence, stress, incontinence, overflow incontinence, functional incontinence, sexual dysfunction, nasal congestion, and CNS disorders selected from the group depression, anxiety, dementia, senility, Alzheimer's, deficiencies in attentiveness and cognition, eating disorders, obesity, bulimia and anorexia, said method comprising administering to a patient in need of such treatment a therapeutically effective amount of a compound of claim 25.

41. A method for treating a disease state comprising urinary incontinence by administering to a subject in need of such treatment an effective amount of a Compound of claim 25.

42. The method of claim 41, wherein the disorder is stress incontinence.

43. The method of claim 41, wherein the disorder is urge incontinence.

44. A method for treating nasal congestion by administering to a mammal in need of such treatment an effective amount of a Compound of claim 25.

45. The method of claim 44, wherein the nasal congestion is sinusitis or otitis.

46. A method for treating sexual dysfunction by administering to a mammal in need of such treatment an effective amount of a Compound of claim 25.

* * * * *